US007687515B2

(12) United States Patent
Cai et al.

(10) Patent No.: US 7,687,515 B2
(45) Date of Patent: Mar. 30, 2010

(54) 6-PHENYL-1H-IMIDAZO[4,5-C]PYRIDINE-4-CARBONITRILE DERIVATIVES

(75) Inventors: Jiaqiang Cai, Newhouse (GB); Zoran Rankovic, Newhouse (GB); Philip Stephen Jones, Newhouse (GB); David Jonathan Bennett, Newhouse (GB); Iain Cumming, Newhouse (GB); Jonathan Gillespie, Newhouse (GB)

(73) Assignee: N.V. Organon, Oss (NL)

( * ) Notice: Subject to any disclaimer, the term of this patent is extended or adjusted under 35 U.S.C. 154(b) by 150 days.

(21) Appl. No.: 11/653,600

(22) Filed: Jan. 16, 2007

(65) Prior Publication Data

US 2007/0179138 A1 Aug. 2, 2007

Related U.S. Application Data

(60) Provisional application No. 60/759,448, filed on Jan. 17, 2006.

(51) Int. Cl.
*A61K 31/5377* (2006.01)
*A61K 31/496* (2006.01)
*A61K 31/4745* (2006.01)
*C07D 471/02* (2006.01)

(52) U.S. Cl. ...................... 514/303; 546/118
(58) Field of Classification Search .................. 546/118; 514/303
See application file for complete search history.

(56) References Cited

U.S. PATENT DOCUMENTS 5,358,953 A * 10/1994 Alker et al. .................. 514/290

FOREIGN PATENT DOCUMENTS

| EP | 1724264 | 11/2006 |
| WO | WO 03/020278 | 3/2003 |
| WO | WO 03/020287 | 3/2003 |
| WO | WO 03/020721 | 3/2003 |
| WO | WO 2004/000819 | 12/2003 |
| WO | WO 2004/000843 | 12/2003 |
| WO | WO 2005/085210 | 9/2005 |

OTHER PUBLICATIONS

Palmer et al., Journal of medicinal chemistry, (Dec. 1, 2005) vol. 48, No. 24, pp. 7520-7534.*
Bossard, et al., "Proteolytic Activity of Human Osteoclast Cathepsin K," *J. Biol. Chem.* 271, 1996, 12517-12524.
Bromme, et al., "Human Cathepsin O2, a Matrix Protein-degrading Cysteine Protease Expressed in Osteoclasts," *J. Biol. Chem.*, 271, 1996, 2126-2132.
Bromme, et al., "Human Cathepsin O2, a Novel Cysteine Protease Highly Expressed in Osteoclastomas and Ovary Molecular Cloning, Sequencing and Tissue Distribution," *Biol. Chem. Hoppe-Seyler*, 376, 1995, 379-384.
Kafienah, et al., "Human cathepsin K cleaves native type I and II collagens at the N-terminal end of the triple helix," *Biochem. J. 331,*, 1998, 727-732.
Nakagawa, et al., "Impaired Invariant Chain Degradation and Antigen Presentation and Diminished Collagen-Induced Arthritis in Cathepsin S Null Mice," *Immunity*, 10, 1999, 207-217.
Shi, et al. Cathepsin S Required for Normal MHC Class II Peptide Loading and Germinal Center Development, *Immunity*, 10, 1999, 197-206.
Sukhova, et al., "Expression of the Elastolytic Cathepsins S and K in Human Atheroma and Regulation of their Production in Smooth Muscle Cells," *J. Clin. Invest. 102*, 1998, 576-583.
Yang, et al., "Cathepsin S Is Required for Murine Autoimmune Myasthenia Gravis Pathogenesis," *J. Immun.*, 174, 2005, 1729-1737.
Zheng, et al., "Inducible targeting of IL-13 to the adult lung causes matrix metalloproteinase-and cathepsin-dependent emphysema," *J. Clin. Invest.*, 106, 2000, 1081-1093.
International Search Report and Written Opinion for International Application No. PCT/EP2007/050356, dated Mar. 16, 2007.

* cited by examiner

*Primary Examiner*—D. Margaret Seaman
*Assistant Examiner*—Niloofar Rahmani
(74) *Attorney, Agent, or Firm*—Susan Hess

(57) ABSTRACT

The present invention relates to 6-phenyl-1H-imidazo[4,5-c]pyridine-4-carbonitrile derivatives having the general Formula I

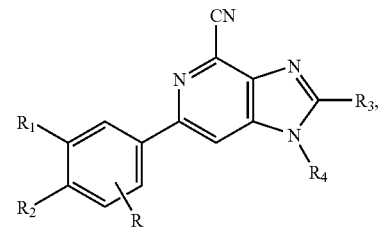

wherein each of the substituents is given the definition as set forth in the specification and claims, pharmaceutical compositions comprising the same as well as to the use of these derivatives for the preparation of a medicament for the treatment of cathepsin S and/or cathepsin K related diseases such as osteoporosis, atherosclerosis, inflammation and immune disorders, such as rheumatoid arthritis, and chronic pain, such as neuropathic pain.

21 Claims, No Drawings

6-PHENYL-1H-IMIDAZO[4,5-C]PYRIDINE-4-CARBONITRILE DERIVATIVES

The invention relates to 6-phenyl-1H-imidazo[4,5-c]pyridine-4-carbonitrile derivatives, to pharmaceutical compositions comprising the same, as well as to the use of these derivatives for the preparation of a medicament for the treatment of cathepsin S and/or cathepsin K related diseases such as osteoporosis, atherosclerosis, inflammation and immune disorders, such as rheumatoid arthritis, and chronic pain, such as neuropathic pain.

Cysteine proteases represent a class of peptidases characterised by the presence of a cysteine residue in the catalytic site of the enzyme, and these proteases are associated with the normal degradation and processing of proteins. Many pathological disorders or diseases are the results of abnormal activity of cysteine proteases such as over expression or enhanced activation. The cysteine cathepsins, e.g. cathepsin B, K, L, S, V, F, are a class of lysosomal enzymes which are implicated in various disorders including inflammation, rheumatoid arthritis, osteoarthritis, osteoporosis, tumors, coronary disease, atherosclerosis, autoimmune diseases and infectious diseases.

Cathepsin S is primarily expressed in antigen presenting cells and plays a major role in antigen presentation by degradation of invariant chain that is associated with the major histocompatibility class II complex. Cathepsin S deficient mice showed marked resistance to the development of collagen-induced arthritis and autoimmune myasthenia gravis (Nakagawa er al., Immunity, 10, 207, 1999; Yang et al., 174, 1729, 2005). Cathepsin S has been shown to degrade all of the major components of the extracellular matrix and has been implicated in the pathogenic response that leads to atherosclerosis, emphysema and chronic obstructive pulmonary disease (Shi et al., Immunity, 10, 197, 1999; Zheng et al., J Clin. Invest., 106, 1081, 2000). Cathepsin S has also been indicated for pain (WO 2003020278).

Cathepsin K has strong collagenolytic, elastase and gelatinase activities (Bromme et al., J. Biol, Chem, 271, 2126-2132,1996) and is predominantly expressed in osteoclasts (Bromme and Okamoto, Biol. Chem. Hopp-Seyler, 376, 379-384, 1995). It cleaves key bone matrix proteins, including collagen type I and II (Kaffienah et al., Biochem. J. 331, 727-732, 1998), gelatine, osteopontin and osteonectin, and as such is involved in extracellular matrix metabolism necessary for normal bone growth and remodelling (Bossard et al., J. Biol. Chem. 271, 12517-12524, 1996). Inhibition of cathepsin K should result in the diminution of osteoclast mediated bone resorption. Cathepsin K inhibitors may therefore represent new therapeutic agents for the treatment of disease states in man such as osteoporosis.

Sukhova et al (J. Clin. Invest. 102, 576-583, 1998) have demonstrated that cells (macrophages) that migrate into and accumulate within developing human atherosclerotic plaques also synthesize the potent elastases Cathepsin K and S. Matrix degradation, particularly in the fibrous cap of such plaques, is a crucial process in atherosclerotic lesion destabilization. Thus, the metabolism of the extracellular matrix components collagen and elastin, which confer structural integrity upon the lesion's fibrous cap, can critically influence the clinical manifestations of atherosclerosis, such as coronary artery thrombosis as a result of rupture of an atherosclerotic plaque. Inhibition of cathepsins K and/or S at sites of plaques prone to rupture may thus represent an effective way of preventing such events. 4-Amino-pyrimidine-2-carbonitrile derivatives have been disclosed as inhibitors of cathepsins K and/or S in the International Patent Application WO 03/020278 (Novartis Pharma GMBH), while structurally related 4-amino-pyrimidine-2 carbonitrile derivatives were recently disclosed in WO 04/000819 (ASTRAZENECA AB) as Cathepsin S inhibitors. Pyrrolo-pyrimidines have likewise been disclosed as cathepsin K and/or S inhibitors in WO 03/020721 (Novartis Pharma GMBH) and WO 04/000843 (ASTRAZENECA AB). Recently, carbonitrile substituted bicyclic nitrogen containing aromatic systems were disclosed in the International Patent Application WO 05/085210 (Ono Pharmaceutical Co.) as cysteine protease inhibitors useful in the treatment of osteoporosis.

There remains a need for further cathepsin inhibitors, especially for compounds having a preferential inhibitory activity for cathepsin S in comparison with cathepsin K.

To that aim the present invention provides 6-phenyl-1H-imidazo[4,5-c]pyridine-4-carbonitrile derivatives having the general Formula I

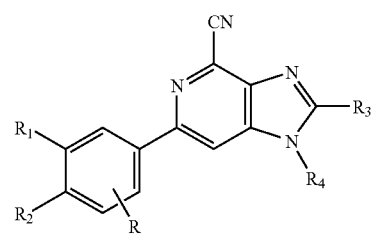

Formula I wherein

R is an optional ortho- or meta-substituent selected from halogen and $(C_{1-4})$alkyloxy;

$R_1$ is $(C_{1-4})$alkyl, $(C_{1-4})$alkyloxy, halogen or $CF_3$;

$R_2$ is H, $(C_{1-4})$alkyl, $(C_{1-4})$alkyloxy or halogen;

$R_3$ is H or $(CH_2)_n$-$NR_5R_6$;

$R_4$ is H or $(C_{1-6})$alkyl, optionally substituted with $COOR_7$ or $NR_8R_9$;

$R_5$ and $R_6$ are independently H, $(C_{3-8})$cycloalkyl, quinuclidin-3-yl, $(C_{2-6})$alkenyl or $(C_{1-6})$alkyl, optionally substituted with halogen, $CF_3$, $(C_{3-4})$cycloalkyl, $(C_{6-10})$aryl, a 5- or 6-membered heteroaryl group, OH, $(C_{1-6})$alkyloxy, $(C_{6-10})$aryloxy, $COOR_{10}$, $CONR_{11}$,$R_{12}$, $NR_{13}R_{14}$ or $NR_{13}SO_2(C_{1-4})$alkyl; or $R_5$ and $R_6$ together with the nitrogen to which they are bound form a 4-8 membered saturated heterocyclic ring, optionally further comprising 1 or more heteroatoms selected from O, S, $SO_2$ and $NR_{15}$, the ring being optionallly substituted with oxo, $(C_{1-4})$alkyl, $(C_{3-8})$cycloalkyl, $NR_{16}$,$R_{17}$ or $CONR_{18}$,$R_{19}$;

$R_7$ is H or $(C_{1-4})$alkyl;

$R_8$ and $R_9$ are independently H, $(C_{1-4})$alkyl (optionally substituted with di($C_{1-4}$)-alkylamino) or $(C_{3-8})$cycloalkyl; or $R_8$ and $R_9$ form together with the nitrogen to which they are bound a 4-8-membered saturated heterocyclic ring, optionally further comprising a heteroatom selected from O and S;

$R_{10}$ is H or $(C_{1-4})$alkyl;

$R_{11}$ and $R_{12}$ are independently H or $(C_{1-4})$alkyl; or $R_{11}$ and $R_{12}$ together with the nitrogen to which they are bound form a 4-8 membered saturated heterocyclic ring, optionally further comprising a heteroatom selected from O and S;

$R_{13}$ and $R_{14}$ are independently H or $(C_{1-4})$alkyl; or $R_{13}$ and $R_{14}$ together with the nitrogen to which they are bound form a 4-8 membered saturated heterocyclic ring, optionally further comprising a heteroatom selected from O and S;

$R_{15}$ is H, $(C_{1-4})$alkyl (optionally substituted with OH, $(C_{1-4})$alkyloxy, di$(C_{1-4})$alkylamino, or $CONR_{21}R_{22}$), phenyl, pyridyl, $COR_{20}$ or $CONR_{21}R_{22}$;

$R_{16}$ and $R_{17}$ are independently H or $(C_{1-4})$alkyl; or $R_{16}$ and $R_{17}$ together with the nitrogen to which they are bound form a 4-8 membered saturated heterocyclic ring, optionally further comprising a heteroatom selected from O and S;

$R_{18}$ and $R_{19}$ are independently H or $(C_{1-4})$alkyl;

$R_{20}$ is H, $(C_{1-4})$alkyl, $(C_{3-8})$cycloalkyl, $(C_{1-4})$alkyloxy or furyl;

$R_{21}$ and $R_{22}$ are independently H or $(C_{1-4})$alkyl; or $R_{21}$ and $R_{22}$ together with the nitrogen to which they are bound form a 4-8 membered saturated heterocyclic ring, optionally further comprising a heteroatom selected from O and S;

n is 0 or 1; or a pharmaceutically acceptable salt thereof.

The compounds are inhibitors of cathepsin S and cathepsin K and can therefor be used for the preparation of a medicament for the treatment of osteoporosis, atherosclerosis, inflammation and immune disorders, such as rheumatoid arthritis, and chronic pain, such as neuropathic pain.

The term $(C_{1-6})$alkyl, as used in the definition of formula I, means a branched or unbranched alkyl group having 1-6 carbon atoms, like hexyl, pentyl, 3-methyl-butyl, butyl, isobutyl, tertiary butyl, propyl, isopropyl, ethyl and methyl. The term $(C_{1-4})$alkyl means a branched or unbranched alkyl group having 1-4 carbon atoms, like butyl, isobutyl, tertiary butyl, propyl, isopropyl, ethyl and methyl.

In the term $(C_{1-6})$alkyloxy $(C_{1-6})$alkyl has the meaning as previously given. The term $(C_{2-6})$alkenyl, as used in the definition of formula I, means a branched or unbranched alkenyl group having 1-6 carbon atoms, like 2-hexenyl, 2-pentenyl, 3-methyl-2-butenyl, 2-propenyl (allyl), 1-methylethenyl (β-allyl) or ethenyl. The term $(C_{3-8})$cycloalkyl means a cycloalkyl group having 3-8 carbon atoms, such as cyclooctyl, cycloheptyl, cyclohexyl, cyclopentyl, cyclobutyl and cyclopropyl. The term quinuclidin-3-yl means 1-aza-bicyclo[2,2,2]oct-3-yl. The term $(C_{6-10})$aryl means a radical derived from an aromatic group having 6-10 carbon atoms like for example phenyl and naphthyl.

The term 5- or 6-membered heteroaryl group as used in the definition of $R_5$ and $R_6$ means an aromatic 5- or 6-membered ring having 1-3 Heteroatoms selected from nitrogen, oxygen and sulfur. Examples of such heteroaryl groups are pyridyl, imidazolyl, pyrazolyl, pyrimidinyl, thiazolyl, isothiazolyl, oxazolyl, isoxazolyl, thienyl, oxadiazolyl, and the like. Preferred heteroaryl groups are 2-pyridy, 3-pyridyl,1,3-thiazol-2-yl, 1,2 oxazol-3-yl and 5-methyl-isoxazol-3-yl.

In the definition of formula I $R_5$ and $R_6$ can form together with the nitrogen to which they are bound a 4-8 membered saturated heterocyclic ring, such as an azetidine, a pyrrolidine, a piperidine, or a 1H-azepine ring. Such rings may contain 1 or more additional heteroatoms selected from O, S, $SO_2$ or $NR_{15}$ to form rings such as a morpholine, a thiomorpholine, a 4-dioxo-4-thiomorpholine, a hexahydro-1,4-oxaze-pine, a piperazine, a homopiperazine, an imidazolidine or a tetrahydrothiazole ring. In the definition of formula I $R_8$ and $R_9$ can form together with the nitrogen to which they are bound a 4-8 membered saturated heterocyclic ring, such as an azetidine, a pyrrolidine, a piperidine or a 1H-azepine ring. Such rings may further comprise a heteroatom selected from O and S to form rings such as a morpholine, a thiomorpholine, a hexahydro-1,4-oxazepine or a tetrahydrothiazole ring.

In the definition of formula I $R_{11}$ and $R_{12}$ can form together with the nitrogen to which they are bound a 4-8 membered saturated heterocyclic ring, such as an azetidine, a pyrrolidine, a piperidine or a 1H-azepine ring. Such rings may further comprise a heteroatom selected from O and S to form rings such as a morpholine, a thiomorpholine, a hexahydro-1,4-oxazepine or a tetrahydrothiazole ring.

In the definition of formula I $R_{13}$ and $R_{14}$ can form together with the nitrogen to which they are bound a 4-8 membered saturated heterocyclic ring, such as an azetidine, a pyrrolidine, a piperidine or a 1H-azepine ring. Such rings may further comprise a heteroatom selected from O and S to form rings such as a morpholine, a thiomorpholine, a hexahydro-1,4-oxazepine or a tetrahydrothiazole ring.

In the definition of formula I $R_{16}$ and $R_{17}$ can form together with the nitrogen to which they are bound a 4-8 membered saturated heterocyclic ring, such as an azetidine, a pyrrolidine, a piperidine or a 1H-azepine ring. Such rings may further comprise a heteroatom selected from O and S to form rings such as a morpholine, a thiomorpholine, a hexahydro-1,4-oxazepine or a tetrahydrothiazole ring.

In the definition of formula I $R_{21}$ and $R_{22}$ can form together with the nitrogen to which they are bound a 4-8 membered saturated heterocyclic ring, such as an azetidine, a pyrrolidine, a piperidine or a 1H-azepine ring. Such rings may further comprise a heteroatom selected from O and S to form rings such as a morpholine, a thiomorpholine, a hexahydro-1,4-oxazepine or a tetrahydrothiazole ring.

The term halogen means F, Cl, Br, or I. When halogen is a substituent at an alkyl group, F is preferred. A preferred halogen substituted alkyl group is trifluoromethyl.

In one embodiment the invention provides compounds according to Formula I wherein R is absent;

$R_1$ is $(C_{1-4})$alkyl, $(C_{1-4})$alkyloxy or $CF_3$;

$R_2$ is H, $(C_{1-4})$alkyl or $(C_{1-4})$alkyloxy;

$R_3$ is H or $(CH_2)_n$-$NR_5R_6$;

$R_4$ is H or $(C_{1-6})$alkyl, optionally substituted with $COOR_7$ or $NR_8R_9$;

$R_5$ and $R_6$ are independently H, $(C_{3-8})$cycloalkyl, $(C_{2-6})$alkenyl or $(C_{1-6})$alkyl, optionally substituted with halogen, $CF_3$, $(C_{3-8})$cycloalkyl, $(C_{6-10})$aryl, a 5- or 6-membered heteroaryl group, OH, $(C_{1-6})$alkyloxy, $(C_{6-10})$aryloxy, $COOR_{10}$, $CONR_{11}R_{12}$ or $NR_{13}R_{14}$; or $R_5$ and $R_6$ together with the nitrogen to which they are bound form a 4-8 membered saturated heterocyclic ring, optionally further comprising 1 or more heteroatoms selected from O, S, $SO_2$ and $NR_{15}$, the ring being optionally substituted with oxo, $(C_{1-4})$alkyl, $NR_{16}R_{17}$or $CONR_{18}R_{19}$;

$R_7$ is H or $(C_{1-4})$alkyl;

$R_8$ and $R_9$ are independently H, $(C_{1-4})$alkyl or $(C_{3-8})$cycloalkyl; or $R_8$ and $R_9$ form together with the nitrogen to which they are bound a 4-8-membered saturated heterocyclic ring, optionally further comprising a heteroatom selected from O and S;

$R_{10}$ is H or $(C_{1-4})$alkyl;

$R_{11}$ and $R_{12}$ are independently H or $(C_{1-4})$alkyl; or $R_{11}$ and $R_{12}$ together with the nitrogen to which they are bound form a 4-8 membered saturated heterocyclic ring, optionally further comprising a heteroatom selected from O and S;

$R_{13}$ and $R_{14}$ are independently H or $(C_{1-4})$alkyl; or $R_{13}$ and $R_{14}$ together with the nitrogen to which they are bound form a 4-8 membered saturated heterocyclic ring, optionally further comprising a heteroatom selected from O and S;

$R_{15}$ is H, phenyl, pyridyl, $COR_{20}$ or $CONR_{21}R_{22}$;

$R_{16}$ and $R_{17}$ are independently H or $(C_{1-4})$alkyl; or $R_{16}$ and $R_{17}$ together with the nitrogen to which they are bound form a 4-8 membered saturated heterocyclic ring, optionally further comprising a heteroatom selected from O and S;

$R_{18}$ and $R_{19}$ are independently H or $(C_{1-4})$alkyl;

$R_{20}$ is H, $(C_{1-4})$alkyl or furyl;

$R_{21}$ and $R_{22}$ are independently H or $(C_{1-4})$alkyl; or $R_{21}$ and $R_{22}$ together with the nitrogen to which they are bound form a 4-8 membered saturated heterocyclic ring, optionally further comprising a heteroatom selected from O and S; and n is 0 or 1;

with the proviso that one of $R_3$ and $R_4$ is H;

or a pharmaceutically acceptable salt thereof.

Preferred in the invention are those compounds according to Formula I wherein $R_1$ is $CF_3$. Further preferred are compounds of formula I wherein $R_2$ is $(C_{1-4})$alkyloxy. Especially preferred are compounds of the invention wherein $R_1$ is $CF_3$ and $R_2$ is ethoxy.

Specifically preferred 6-phenyl-1H-imidazo[4,5-c]pyridine-4-carbonitrile derivatives of the invention are:

6-(4-ethoxy-3-trifluoromethyl-phenyl)-1H-imidazo[4,5-c]pyridine-4-carbonitrile;

[4-cyano-6-(4-ethoxy-3-trifluoromethyl-phenyl)-imidazo[4,5-c]pyridin-1-yl]-acetic acid;

[4-cyano-6-(4-ethoxy-3-trifluoromethyl-phenyl)-imidazo[4,5-c]pyridin-1-yl]-butyric acid;

6-(4-ethoxy-3-trifluoromethyl-phenyl)-2-(3-oxo-piperazine-1-ylmethyl) -1H-imidazo-[4,5,c]pyridine-4-carbonitrile;

2-(1,1-dioxo-thiazolidin-3-ylmethyl)-methyl]-6-(4-ethoxy-3-trifluoromethyl-phenyl)-1H-Imidazo[4,5-c]pyridine-4-carbonitrile;

6-(4-ethoxy-3-trifluoromethyl-phenyl)-1-(2-morpholin-4-yl-ethyl)-1H-imidazo[4,5-c]-pyridine-4-carbonitrile;

6-(4-ethoxy-3-trifluoromethyl-phenyl)-1-(2-piperidin-1-yl-ethyl)-1H-imidazo[4,5-c]-pyridine-4-carbonitrile;

1-(2-dimethylamino-ethyl)-6-(4-ethoxy-3-trifluoromethyl-phenyl)-1H-imidazo[4,5-c]-pyridine-4-carbonitrile;

6-(4-ethoxy-3-trifluoromethyl-phenyl)-1-(3-morpholin-4-yl-propyl)-1H-imidazo[4,5-c]-pyridine-4-carbonitrile;

1-(3-dimethylamino-propyl)-6-(4-ethoxy-3-trifluoromethyl-phenyl)-1H-imidazo[4,5-c]-pyridine-4-carbonitrile;

6-(4-ethoxy-3-trifluoromethyl-phenyl)-2-(4-methyl-piperazin-1-ylmethyl)-1H-imidazo-[4,5-c]pyridine-4-carbonitrile; and 6-(4-ethoxy-3-trifluoromethyl-phenyl)-2-[(2-hydroxy-ethylamino)-methyl]-1H-imidazo[4,5-c]pyridine-4-carbonitrile;

1-ethyl-2-(pyridin-4-ylaminomethyl)-6-(3-trifluoromethyl-phenyl)-1H-imidazo[4,5-c]pyridine-4-carbonitrile;

6-(4-ethoxy-3-trifluoromethyl-phenyl)-2-[4-(2-hydroxy-ethyl)-3-oxo-piperazin-1-ylmethyl]-1H-imidazo[4,5-c]pyridine-4-carbonitrile;

6-(4-ethoxy-3-trifluoromethyl-phenyl)-2-(4-oxo-imidazolidin-1-ylmethyl)-1H-imidazo[4,5-c]pyridine-4-carbonitrile or a pharmaceutically acceptable salt thereof.

The invention provides in a further aspect pharmaceutical compositions comprising a 6-phenyl-1H-imidazo[4,5-c]pyridine-4-carbonitrile derivative having general formula I, or a pharmaceutically acceptable salt thereof, in admixture with pharmaceutically acceptable auxilliaries.

The 6-phenyl-1H-imidazo[4,5-c]pyridine-4-carbonitrile derivatives of general Formula I may be prepared by, as depicted in Scheme 1, selective cyanation of 4-amino-2,6-dichloro-3-nitropyridine (II) with copper cyanide to produce 4-amino-6-chloro-2-cyano-3-nitropyridine (III). Palladium catalysed cross coupling of intermediate (III) with aryl boronic acids or aryltin compounds, wherein the aryl groups are substituted with R, $R_1$ and $R_2$, each having the meaning as previously defined, gives 4-amino-2-cyano-3-nitro-6-phenylpyridine derivaties of formula (IV) as product. Reduction of the nitro group of intermediate (IV) by Fe powder or $SnCl_2$ at acidic conditions or palladium catalysed hydrogenation provides a 2-cyano-3,4-diamino-6-phenylpyridine derivaitve of formula (V) as the product. Treatment of compound (V) with triethyl orthoformate in the presence of a Lewis acid catalyst, e.g. ytterbium triflate, provides a 6-phenyl-1H-imidazo[4,5-c]pyridine-4-carbonitrile derivative of formula (VI). Further derivatisation from the $N^1$-position of compounds of formula (VI) can be achieved by direct alkylation under basic conditions with a compound of formula $R_4X$, wherein $R_4$ has the meaning as previously defined and wherein X is a leaving group, such as Br, Cl, OMs or OTf, or by alkylation under Mitsunobu conditions with a compound of formula $R_4X$, wherein X equals OH.

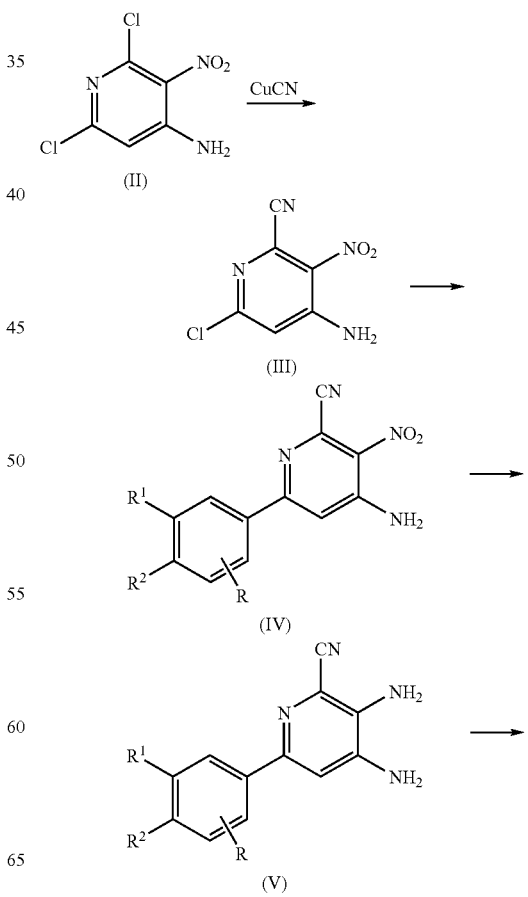

Scheme 1

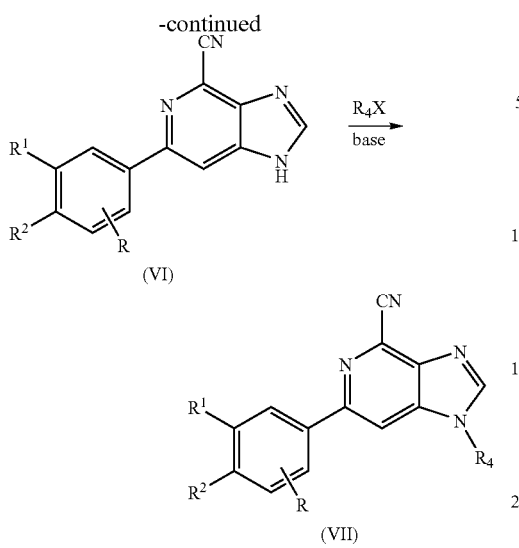

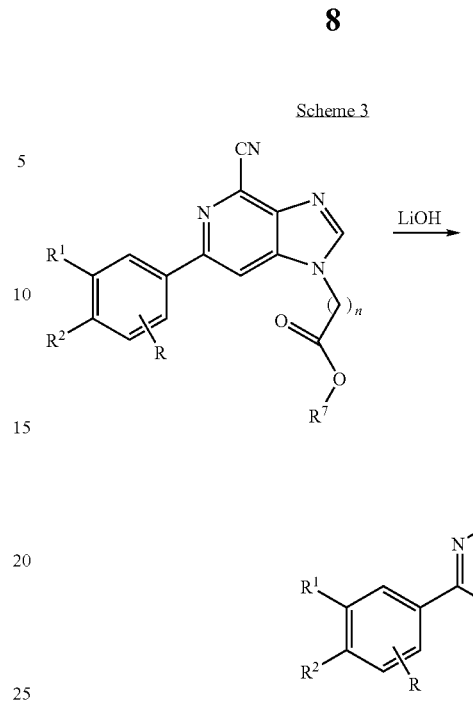

The 6-phenyl-1H-imidazo[4,5-c]pyridine-4-carbonitrile derivatives of general Formula I, wherein $R_4$ represents a $(C_{1-6})$alkyl group substituted with $NR_8R_9$, can advantageously be prepared starting from the corresponding bromide derivative of formula VIII (Scheme 2), wherein R, $R_1$ and $R_2$ have the meaning as previously defined and wherein m is 1-5. Direct replacement of bromide of compound (VIII) with either primary or secondary amine in a suitable solvent, such as dimethylsulfoxide, dimethylformamide, methanol or tetrahydrofuran at an appropriate temperature provides compound with general formula (IX) as the product.

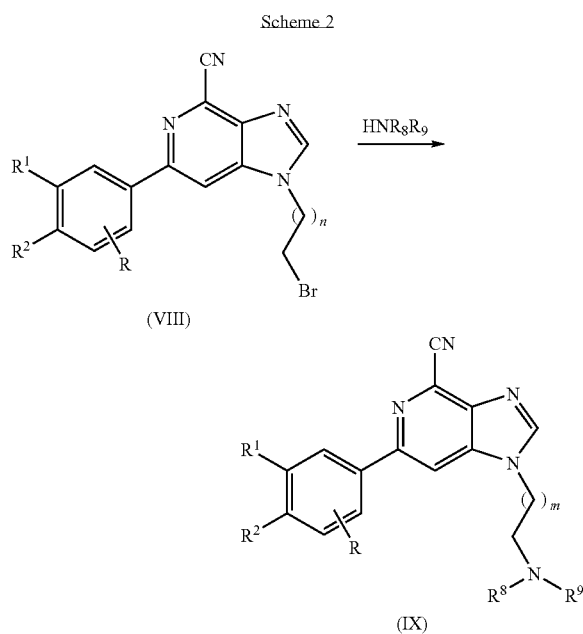

The 6-phenyl-1H-imidazo[4,5-c]pyridine-4-carbonitrile derivatives of general Formula I, wherein $R_4$ represents a $(C_{1-6})$alkyl group substituted with a carboxylic acid function, can advantageously be prepared starting from the corresponding ester derivative by lithium hydroxide or sodium hydroxide promoted hydrolysis as depicted in scheme 3.

In an alternative method for the introduction of an amino group at the 2-position of the 1H-imidazo[4,5-c]pyridine moiety, a compound having the formula (XII) can be synthesised by the route as depicted in scheme 4. Nitro group reduction of 4-amino-6-chloro-2-cyano-3-nitropyridine (Ill) by either Fe or $SnCl_2$ under acidic conditions or palladium catalysed hydrogenation provides 6-chloro-2-cyano-3,4-diaminopyridine (X) as product. Treatment of compound (X) with dichloromethylene-N,N'-$R_5R_6$-substituted ammonium chloride, wherein $R_5$ and $R_6$ have the meaning as previously defined, in chloroform/acetonitrile at reflux temperature produces a 2-amino-6-chloro-4-cyano-1H-imidazo[4,5-c]pyridine derivatitve of formula (XI). Palladium or other transition metal catalysed cross coupling of a compound of formula (XI) with either aryl boronic acid or aryltin, wherein the aryl groups are substituted with R, $R_1$ and $R_2$, having the meaning as previously defined, affords a 2-amino-6-phenyl-1H-imidazo-[4,5-c]pyridine-4-carbonitrile derivative of formula (XII) as desired product.

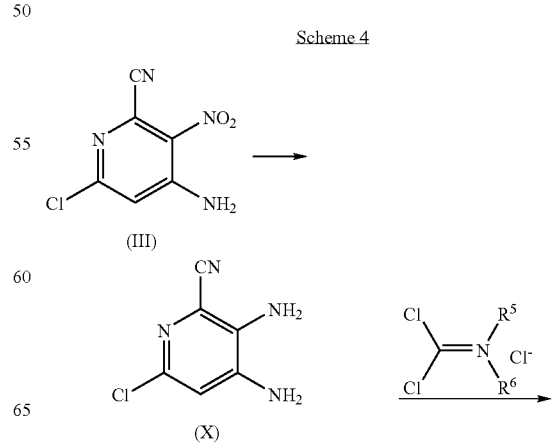

-continued

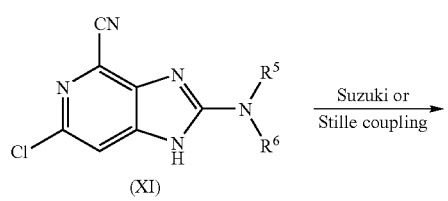

(XI)

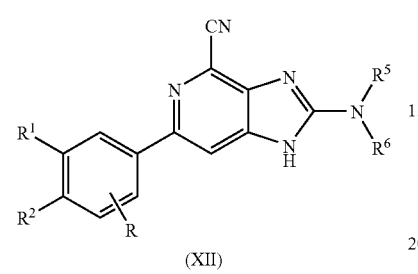

(XII)

Scheme 6

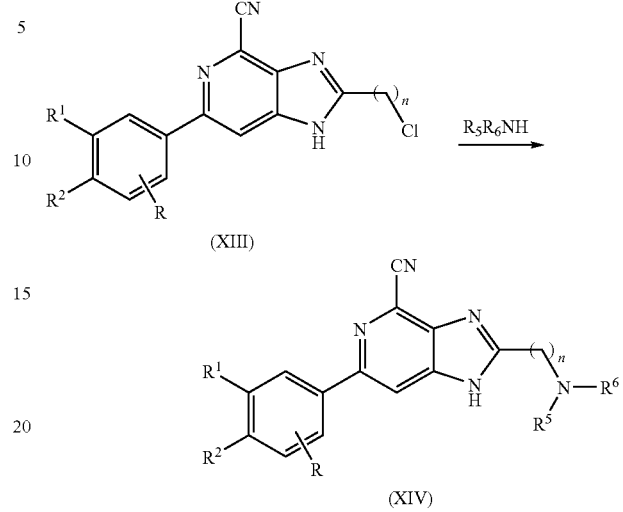

(XIII)

(XIV)

In yet another method, for the introduction of a R₃ group at the 2-position of the 1H-imidazo[4,5-c]pyridine moiety, a compound having the formula (XIII) can be synthesised by condensation of a 2-cyano-3,4-diamino-6-phenylpyridine derivative of formula (V), wherein R, $R_1$ and $R_2$ have the previously defined meaning, with an appropriate acid, acyl chloride, orthoformate or aldehyde under various conditions as depicted in scheme 5.

In a yet another method, the compounds of general structure XIV, where n=3, can be advantageously prepared from compound XIII where n=1 by the method as depicted in scheme 7. Reaction of XIII with triphenylphosphine in a suitable solvent, e.g. acetonitrile, provides Wittig reagent XV. Wittig reaction of XV with chloroacetaldehyde in the presence of 1,8-diazabicyclo[5.4.0]undec-7-ene (DBU) as base gives substituted allyl chloride XVI as product. Substitution of chloride provides compounds XVII and hydrogenation of XVII using palladium on charcoal as catalyst gives compounds XIV where n=3.

Scheme 5

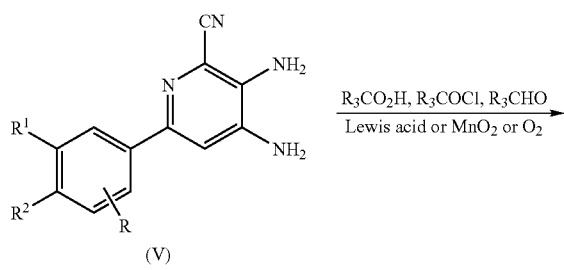

(V)

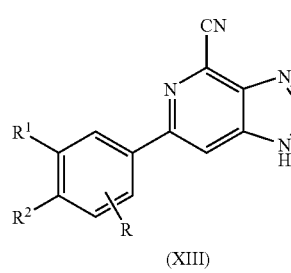

(XIII)

The 6-phenyl-1H-imidazo[4,5-c]pyridine-4-carbonitrile derivatives of general Formula I, wherein R₃ represents a (C₁₋₆)alkyl group substituted with NR₅R₆, can advantageously be prepared starting from the corresponding chloro-substituted alkyl derivative of formula XIII as depicted in scheme 6. Substitution of chloride of compounds (XIII) with various primary or secondary amines provides the desired product (XIV).

Scheme 7

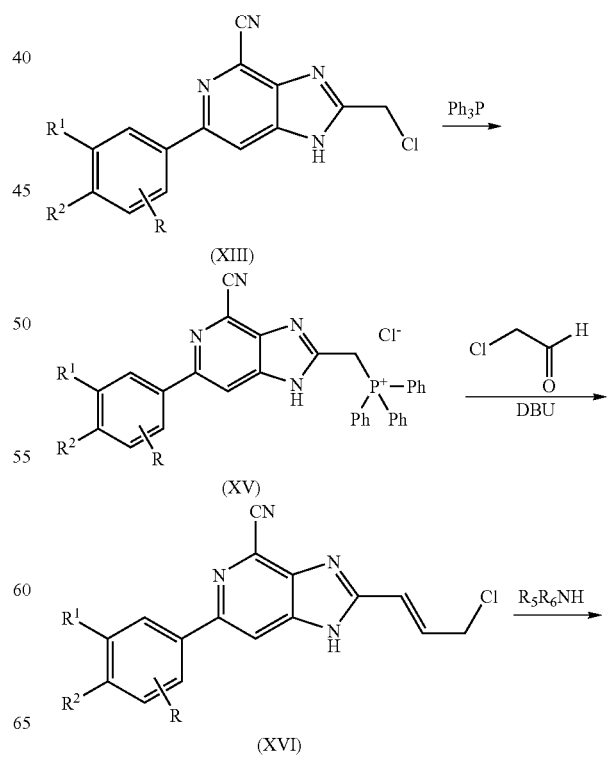

(XIII)

(XV)

(XVI)

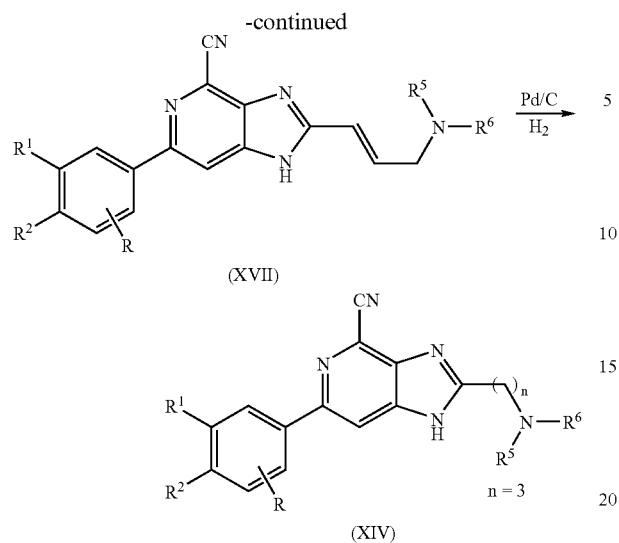

(XVII)

(XIV) n = 3

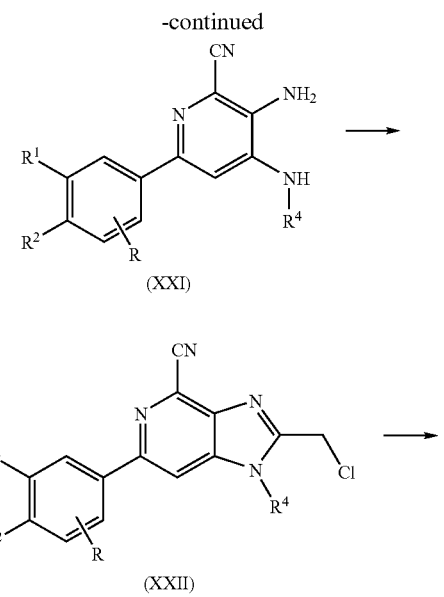

(XXI)

(XXII)

(XXIII)

The 6-phenyl-1H-imidazo[4,5-c]pyridine-4-carbonitrile derivatives of general Formula I, where both $R_3$ and $R_4$ are not hydrogen, can be prepared according the scheme 8. Alkylation of compound III using alkyl iodide or bromide and potassium carbonate as base in a suitable solvent, e.g. acetonitrile or DMF gives compound XIX as product. Suzuki coupling of XIX with an aryl boronic acid using palladium derivatives as catalyst gives compound XX as product. Reduction of nitro to $NH_2$ of compound XX using the method as described in scheme 1 affords compound XXI. Cyclisation using the method as described in scheme 5 gives product XXII and chloride replacement with an amine by the method as shown in scheme 6 provides desired compounds XXIII.

In a yet another method, compounds with different R, $R_1$ and $R_2$ of general Formula I can be prepared by the synthetic route depicted in scheme 9. Reduction of compound XIX using the method described in scheme 1 gives compound XXIV. Imidazole ring formation by the method of scheme 5 provides compound XXV. Suzuki coupling of XXV with various aryl boronic acid gives desired product as described by generic Formula I.

Scheme 8

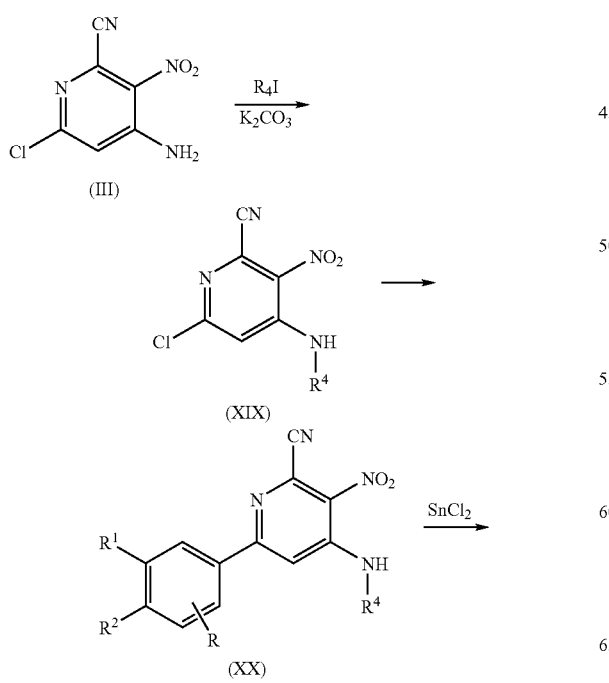

Scheme 9

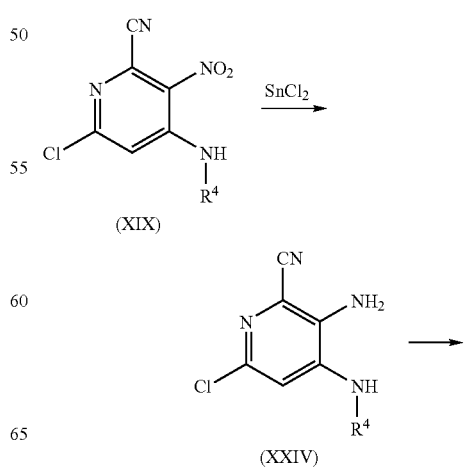

-continued

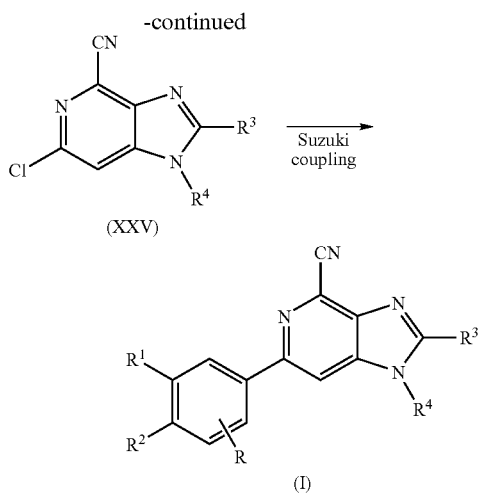

In the preparation of a 6-phenyl-1H-imidazo[4,5-c]pyridine-4-carbonitrile derivative of general Formula I in which the $R_3$ or the $R_4$ group contains a basic amino nitrogen atom (either in the form of $NR_5R_6$ or $NR_7R_8$), such a nitrogen is to be temporarily protected, such as for example by the acid labile t-butyloxycarbonyl (Boc) protecting group. Other suitable protecting groups for functional groups which are to be temporarily protected during syntheses, are known in the art, for example from Wuts, P. G. M. and Greene, T. W.: *Protective Groups in Organic Synthesis*, Third Edition, Wiley, New York, 1999.

The 6-phenyl-1H-imidazo[4,5-c]pyridine-4-carbonitrile derivatives of the invention, which can be in the form of a free base, may be isolated from the reaction mixture in the form of a pharmaceutically acceptable salt. The pharmaceutically acceptable salts, such as acid addition salts, may further be obtained by treating the free base of Formula I with an organic or inorganic acid such as, but not limited to, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulphonic acid, fumaric acid, succinic acid, tartaric acid, citric acid, benzoic acid and ascorbic acid.

Suitable salts of 6-phenyl-1H-imidazo[4,5-c]pyridine-4-carbonitrile derivatives of Formula I in which a carboxylate group is present can be an alkali metal salts, such as sodium, potassium or lithium salt, or may be a salt obtained from the combination with an organic base, such as trimethylamine, triethylamine and the like.

Compounds of the invention may exist in solvated as well as in unsolvated forms, including hydrated forms. In general, the solvated forms are equivalent to unsolvated forms and are intended to be encompassed within the scope of the present invention. Compounds of the present invention may exist as amorphous forms, but also multiple crystalline forms may be possible. In general, all physical forms are equivalent for the uses contemplated by the present invention and are intended to be within the scope of this invention.

The 6-phenyl-1H-imidazo[4,5-c]pyridine-4-carbonitrile derivatives of the invention and their salts may contain a centre of chirality in one or more of the side chains $R_1$, $R_2$, $R_4$-$R_{14}$, $R_{20}$-$R_{22}$, and may therefore be obtained as a pure enantiomer, or as a mixture of enantiomers, or as a mixture containing diastereomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

The compounds of the invention were found to be inhibitors of human Cathepsin S and of Cathepsin K and can therefore in a further aspect of the invention be used in therapy, and especially for the preparation of a medicament for the treatment of autoimmune disease, chronic obstructive pulmonary disease, pain, osteoporosis, atherosclerosis and related Cathepsin S and K dependent disorders, such as asthma and IBD.

The compounds of the invention may be administered enterally or parenterally, and for humans preferably in a daily dosage of 0.001-100 mg per kg body weight, preferably 0.01-10 mg per kg body weight. Mixed with pharmaceutically suitable auxiliaries, e.g. as described in the standard reference, Gennaro et al., Remington's Pharmaceutical Sciences, (20th ed., Lippincott Williams & Wilkins, 2000, see especially Part 5: Pharmaceutical Manufacturing) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

Methods

General Chemical Procedures.

All reagents were either purchased from common commercial sources or synthesised according to literature procedures using commercial sources. Proton NMR ($^1$H NMR) were obtained on a Bruker DPX 400 spectrometer and are referenced to internal TMS. Mass spectra were recorded on a Shimadzu LC-8A (HPLC) PE Sciex API 150EX LCMS. Analytical reversed-phase LCMS analysis was carried out on LUNA C18 column (5 μm; 30×4.6 mm) under gradient conditions (90% water/0.1% formic acid to 90% acetonitrile/ 0.1% formic acid) at a flow rate of 4 ml/min.

Abbreviations

Dimethylformamide (DMF), N-methylpyrolidinone (NMP), dichloromethane (DCM), dimethylsulfoxide (DMSO), tetrahydrofuran (THF), 1,2-dimethoxyethane (DME), high pressure liquid chromatography (HPLC), diisopropylethylamine (DIPEA), triethylamine (TEA), broad (br), singlet (s), doublet (d), triplet (t), trifluoroacetic acid (TFA), tert-butyloxycarbonyl (Boc), methanesulphonate (MsO), trifluoromethane-sulphonate (TfO).

EXAMPLE 1.

6-(4-Ethoxy-3-trifluoromethyl-phenyl)-1H-imidazo [4.5-c]pyridine-4-carbonitrile

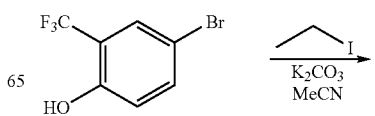

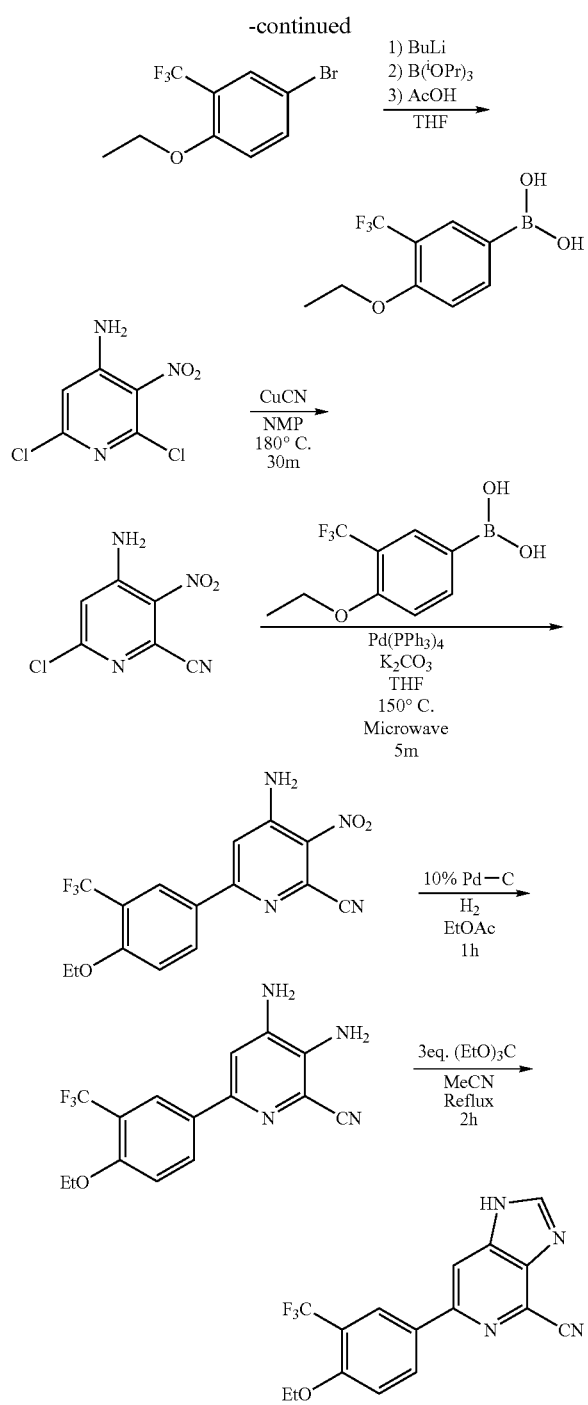

A: 4-Bromo-1-ethoxy-3-trifluoromethyl-benzene

A stirred suspension of 4-bromo-3-trifluoromethyl-phenol (117.6 g, 0.49 mol) iodoethane (77.6 g, 0.49 mol) and potassium carbonate (101.2 g, 0.73 mol) in acetonitrile (600 ml) was heated to reflux for 2.5 hours. The mixture was concentrated under reduced pressure before partitioning between dichloromethane (1 litre) and water (1 litre). The organic phase was collected and dried over magnesium sulfate before concentration under reduced pressure to afford 4-bromo-1-ethoxy-3-trifluoromethyl-benzene (126.97 g). $^1$H NMR (CDCl$_3$): δ 7.66 (s, 1H) 7.56 (d, 1H) 6.86 (s, 1H) 4.09 (q, 2H) 1.44 (t, 3H).

B: 4-Ethoxy-3-trifluoromethylphenylboronic acid

A solution of 4-bromo-1-ethoxy-3-trifluoromethyl-benzene (21.25 g, 90.8 mmol) in dry tetrahydrofuran (120 ml) was purged with nitrogen, cooled to −78° C. and BuLi (2.5 M solution in hexanes, 39.96 ml, 99.9 mmol) added dropwise maintaining a temperature below −70° C. The mixture was stirred for 5 minutes before addition of triisopropyl borate (17.9 g, 95.36 mmol) in one portion. Stirring was continued at −78° C. for 30 minutes before allowing to come to room temperature. The reaction was quenched by addition of 10 ml of acetic acid dissolved in 150 ml water before concentration under reduced pressure to remove tetrahydrofuran. The precipitate was collected by filtration, dissolved in ethyl acetate and dried over sodium sulfate. Purification was achieved by recrystalisation from ethyl acetate/hexane mixtures to afford 4-ethoxy-3-trifluoromethylphenylboronic acid (10 g). $^1$H NMR (DMSO$_{d6}$): δ 8.08 (s, 1H) 8.01 (d, 1H) 7.2 (d, 1H) 4.18 (q, 2H) 1.34 (t, 3H).

C: 4-Amino-6-chloro-3-nitro-pyridine-2-carbonitrile

A stirred suspension of 4-amino-1,6-dichloro-3-nitro-pyridine (17.5 g, 84.1 mmol) and copper (i) cyanide (15.1 g, 168.3 mmol) in 170 ml of 1-methyl-2-pyrrolidinone was lowered into an oil bath preheated to 180° C. and stirring continued for 30 minutes. The mixture was allowed to cool and diluted with ethyl acetate (700 ml) and water (700 ml) and the resultant suspension filtered. The organic layer was separated and further washed with water (500 ml) and 0.1N HCl (500 ml). The organic layer was then dried over sodium sulfate, filtered and concentrated under reduced pressure to give a brown solid which was washed with diethylether and dichloromethane to afford 4-amino-6-chloro-3-nitro-pyridine-2-carbonitrile (8 g).

$^1$H NMR (DMSO): δ 8.8-7.7 (bs, 2H), 7.18 (s, 1H).

D: 4-Amino-6-(4-ethoxy-3-trifluoromethyl-phenyl)-3-nitro-pyridine-2-carbonitrile A stirred mixture 4-amino-6-chloro-3-nitro-pyridine-2-carbonitrile (1 g, 5.04 mmol), 4-ethoxy-3-trifluoromethylphenylboronic acid (1.33 g, 6.04 mmol), tetrakis-(triphenylphosphine)palladium(0) (~500 mg,10 mol %), potassium carbonate (2.09 g, 15.12 mmol) and THF (10 ml) was degassed under a stream of nitrogen before heating in the "Smith" microwave at 150° C. for 10 minutes. The crude mixture was concentrated under reduced pressure to remove THF before partitioning between ethyl acetate and water. The organic layer was separated, dried over sodium sulfate and concentrated under reduced pressure to give a dark brown oil. Trituration with diethylether gave a light brown solid which was filtered and dried under a stream of air to afford 4-amino-6-(4-ethoxy-3-trifluoromethyl-phenyl)-3-nitro-pyridine-2-carbonitrile (900 mg). $^1$H NMR (DMSO): δ 8.25-8.1 (m, 3H), 7.63 (s, 1H), 7.44 (d, 2H), 4.27 (q, 2H), 1.38 (t, 3H).

E: 3,4-Diamino-6-(4-ethoxy-3-trifluoromethyl-phenyl)-pyridine-2-carbonitrile

To a flask containing 4-amino-6-(4-ethoxy-3-trifluoromethyl-phenyl)-3-nitro-pyridine-2-carbonitrile (5 g, 14.2 mmol) and 10% Pd-C (wet) (5 g) under nitrogen was added ethyl acetate (500 ml). The vessel was purged with hydrogen and stirred at room temperature for 1.5 h before filtration through a cellite pad followed by concentration under reduced pressure to afford 3,4-diamino-6-(4-ethoxy-3-trifluoromethyl-phenyl)-pyridine-2-carbonitrile (2.5 g). $^1$H NMR (DMSO): δ 8.02 (m, 2H), 7.31 (d, 1H), 7.14 (s, 1H), 6.1 (bs, 2H), 5.69 (bs, 2H), 4.25 (q, 2H), 1.35 (t, 3H). MS m/z 323.3 (M+1).

F: 6-(4-Ethoxy-3-trifluoromethyl-phenyl)-1H-imidaza[4,5-c]pyridine-4-carbonitrile A stirred suspension of 3,4-diamino-6-(4-ethoxy-3-trifluoromethyl-phenyl)-pyridine-2-carbonitrile (4.4 g, 13.7 mmol), ytterbium triflate (173 mg, 2 mol %), triethylorthoformate (6.08 g, 41.1 mmol) and acetonitrile (50 ml) was heated to reflux for 30 minutes. The solid precipitate was collected by filtration and washed sparingly with acetonitrile to afford 6-(4-ethoxy-3-trifluoromethyl-phenyl)-1H-imidazo[4,5-c]pyridine-4-carbonitrile (2.6 g). $^1$H NMR (DMSO): δ 8.67 (s, 1H), 8.47 (s, 1H), 8.36 (m, 2H), 7,49 (d, 1H), 4.26 (q, 2H), 1.38 (t, 3H). MS m/z 333.3(M+1).

EXAMPLE 2

[4-Cyano-6-(4-ethoxy-3-trifluoromethyl-phenyl)-imidazo[4.5-c]pyridin-1-yl]-acetic acid methyl ester

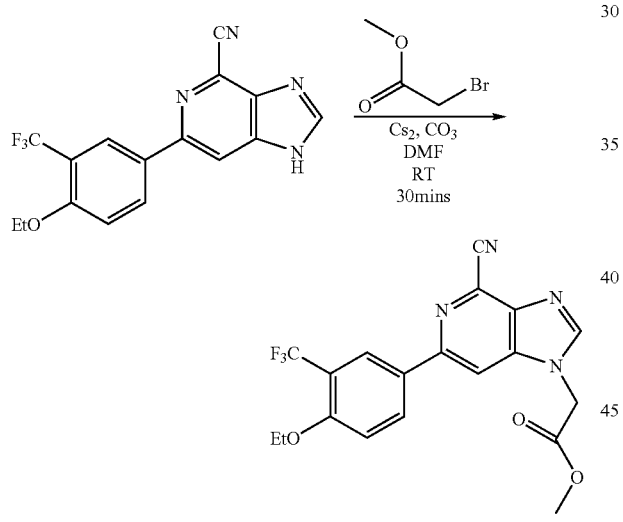

To a solution of 6-(4-ethoxy-3-trifluoromethyl-phenyl)-1H-imidazo[4,5-c]-pyridine-4-carbonitrile (Example 1; 200 mg, 0.6 mmol) and methyl bromoacetate (276.2 mg, 1.81 mmol) in dimethylformamide (4 ml) was added cesium carbonate (325.5 mg, 1.81 mmol) and the mixture stirred at room temperature for 30 minutes. The mixture was concentrated under reduced pressure to remove the dimethylformamide before partitioning between ethyl acetate (200 ml) and water (200 ml). The organic layer was collected and dried over sodium sulfate before purification on a 10 g silica column eluting with diethylether. The product was then washed sparingly with diethylether and dried under a stream of air to afford [4-cyano-6-(4-ethoxy-3-trifluoromethyl-phenyl)-imidizo[4,5-c]pyridin-1-yl]-acetic acid methyl ester (110 mg). $^1$H NMR (DMSO): δ 8.76 (s, 1H) 8.64 (s,1H) 8.39 (d, 1H) 8.36 (s, 1H) 7.44 (s, 1H) 5.44 (s, 2H) 4.27 (q, 2H) 3.75 (s, 3H) 1.38 (t, 3H). MS m/z 405.7 (M+1).

EXAMPLE 3

[4-Cyano-6-(4-ethoxy-3-trifluoromethyl-phenyl)-imidazo[4,5-c]pyridin-1-yl]-acetic acid To a solution of [4-cyano-6-(4-ethoxy-3-trifluoromethyl-phenyl)-imidazo[4,5-c]-pyridin-1-yl]-acetic acid methyl ester (110 mg, 0.27 mmol) in a 1:1 mixture of dimethylformamide (2 ml) and water (2 ml) was added lithium hydroxide (19 mg, 0.81 mmol) dissolved in 200 μL of water. An additional 2 ml of dimethylformamide was added to aid solubility. The mixture was stirred at room temperature for 30 minutes before acidification to pH 1 with 2N HCl solution and filtration. The solid obtained was washed with ether before dissolving in acetone and concentration under reduced pressure to remove residual organic solvents and afford [4-cyano-6-(4-ethoxy-3-trifluoromethyl-phenyl)-imidazo[4,5-c]pyridin-1-yl]-acetic acid (100 mg). $^1$H NMR (DMSO): δ 8.76 (s, 1H) 8.64 (s, 1H) 8.37 (m, 3H) 7.43 (d, 1H) 5.31 (s, 2H) 4.27 (q, 2H) 1.38 (t, 3H); MS m/z 391.7 (M+1).

EXAMPLE 4

[4-Cyano-6-(4-ethoxy-3-trifluoromethyl-phenyl)-imidazo[4,5-c]pyridin-1-yl]-butyric acid This compound was from 6-(4-ethoxy-3-trifluoromethyl-phenyl)-1H-imidazo-[4,5-c]pyridine-4-carbonitrile (Example 1) with the use of methyl 4-bromobutyrate instead of methyl bromoacetate and using the methods described in examples 2 and 3. $^1$H NMR (DMSO): δ 8.69 (m, 2H) 8.43-8.38 (m, 2H) 7.42 (d, 1H) 4.44 (t, 2H) 4.27 (q, 2H) 2.29 (t, 2H) 2.11 (m, 2H) 1.38 (t, 3H). MS m/z 419.5 (M+1).

EXAMPLE 5a 6-(4-Ethoxy-3-trifluoromethyl-phenyl)-2-(isobutylamino-methyl)-1H-imidazo[4,5,c]pyridine-4-carbonitrile

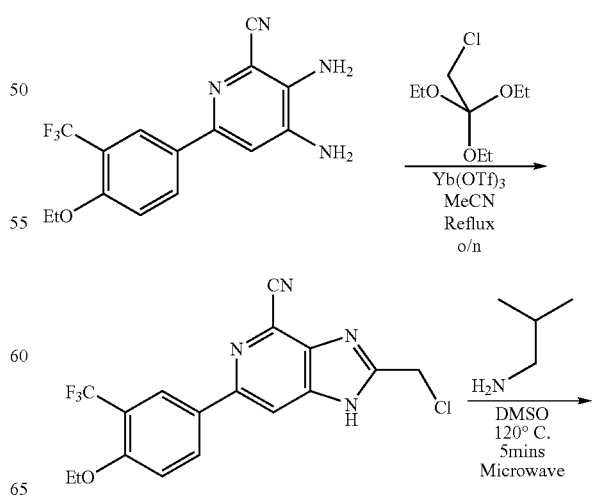

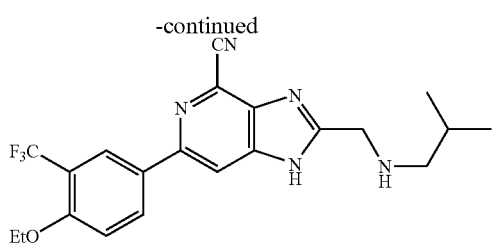

A: 2-Chloromethyl-6-(4-ethoxy-3-Trifluoromethyl-phenyl)-1H-imidazo[4,5,c]pyridine-4-carbonitrile To a solution of 3,4-diamino-6-(4-ethoxy-3-trifluoromethyl-phenyl)-pyridine-2-carbonitrile (1.86 g, 5.78 mmol) and 2-chloro-1,1,1-triethoxyethane (3.41 g, 17.3 mmol) in acetonitrile (40 ml) was added ytterbium triflate (180 mg, 5 mol %) and the mixture heated to reflux overnight. The mixture was concentrated under reduced pressure before partitioning between ethyl acetate and water. The organic layer was dried over sodium sulfate and concentrated before addition of diethylether. The precipitate was filtered and dried under a stream of air to afford 6-(4-ethoxy-3-trifluoromethyl-phenyl)-2-(chloromethyl)-1H-imidazo[4,5,c]pyridine-4-carbonitrile (1.2 g). ¹H NMR (DMSO): δ 8.42 (s, 1H) 8.38 (d, 1H) 8.34 (s, 1H) 7.40 (d, 1H) 5.05 (s, 2H) 4.26 (q, 2H) 1.38 (t, 3H). MS m/z 381.1 (M+1)

B: 6-(4-Ethoxy-3-trifluoromethyl-phenyl)-2-(isobutylamino-methyl)-1H-imidazo[4,5,c]-pyridine-4-carbonitrile A solution of 2-chloromethyl-6-(4-ethoxy-3-trifluoromethyl-phenyl)-1H-imidazo[4,5,c]pyridine-4-carbonitrile (20 mg, 0.06 mmol) and isobutylamine (21 mg, 0.3 mmol) in dimethylsulfoxide (500 µL) was heated in the Creator microwave at 120° C. for 5 minutes. The mixture was filtered and purified by preparative HPLC to afford 6-(4-Ethoxy-3-Trifluoromethyl-phenyl)-2-(isobutylamino-methyl)-1H-imidazo-[4,5,c]pyridine-4-carbonitrile (11.6 mg). ¹H NMR (MeOD) δ 8.31 (s, 1H) 8.28-8.26 (m, 2H) 7.28 (d, 1H) 4.45 (s, 2H) 4.23 (q, 2H) 3.13 (d, 2H) 2.16 (m, 1H) 1.45 (t, 3H) 1.11 (d, 6H). MS m/z 418.6 (M+1).

The procedure described in Example 5B was further applied, using the appropriate amine derivatives, to prepare the following compounds:

5b: 6-(4-Ethoxy-3-trifluoromethyl-phenyl)-2-[(2-phenoxy-ethylamino-methyl)-1H-imidazo[4,5,c]pyridine-4-carbonitrile ¹H NMR (MeOD) δ 8.3-8.25 (m, 3H) 7.32-7.26 (m, 3H) 7.03-6.96 (m, 3H) 4.78 (s, 2H) 4.39 (t, 2H) 4.23 (q, 2H) 3.76 (t, 2H) 1.45 (t, 3H). MS m/s 482.4 (M+1).

5c: 2-(3-Acetamido-pyrrolidin-1-ylmethyl)-6-(4-ethoxy-3-trifluoromethyl-phenyl)-1H-imidazo[4,5,c]pyridine-4-carbonitrile ¹H NMR (MeOD) δ 8.29-8.24 (m, 3H) 7.27 (d, 2H) 4.92 (s, 2H) 4.51 (m, 1H) 4.23 (q, 2H) 3.96-3.85 (m, 2H) 3.75-3.61 (m, 2H) 2.54 (m, 1H) 2.19 (m, 1H) 1.99 (s, 3H), 1.46 (t, 3H). MS m/z 473.3 (M+1).

5d: 6-(4-Ethoxy-3-trifluoromethyl-phenyl)-2-(3-oxo-piperazine-1-ylmethyl)-1H-imidazo[4,5,c]pyridine-4-carbonitrile ¹H NMR (DMSO) δ 8.36-8.31 (m, 3H) 7.81 (s, NH) 7.39 (d, 1H) 4.26 (q, 2H) 3.98 (s, 2H) 3.21-3.15 (m, 4H) 2.73 (m, 2H) 1.38 (t, 3H). MS m/z 445.5 (M+1).

5e: 6-(4-Ethoxy-3-trifluoromethyl-phenyl)-2-{[2-(2-oxo-imidazolidin-1yl)ethylamino]-methyl}1H-imidazo[4,5,c]pyridine-4-carbonitrile ¹H NMR (MeOD) δ 8.29-8.24 (m, 3H) 7.27 (d, 1H) 4.73 (s, 2H) 4.22 (q, 2H) 3.64-3.47 (m, 8H) 1.45 (t, 3H). MS m/z 474.3 (M+1).

5f: 6-(4-ethoxy-3-trifluoromethyl-phenyl)-2-[(N,N-dimethylcarbamoylmethylamino)-methyl]-1H-imidazo[4,5-c]pyridine-4-carbonitrile ¹H NMR (MeOD) δ 8.31-8.26 (m, 3H) 7.28 (d, 1H) 4.72 (s, 2H) 4.35 (s, 2H) 4.26 (q, 2H) 3.05 (s, 3H) 3.03 (s, 3H) 1.46 (t, 3H). MS m/z 447.3 (M+1).

5g: 2-(1,1-dioxo-thiazolidin-3-ylmethyl)-methyl]-6-(4-ethoxy-3-trifluoromethyl-phenyl)-1H-Imidazo[4,5-c]pyridine-4-carbonitrile ¹H NMR (MeOD) δ 8.30-8.22 (m, 3H) 7.28 (d, 1H) 4.54 (s, 2H) 4.23 (q, 2H) 4.22 (m, 1H) 4.13 (m, 1H) 3.56 (m, 1H) 3.40 (m, 1H) 3.24 (m , 2H) 2.17 (m, 1H) 2.33 (m, 1H) 1.45 (t, 3H). MS m/z 480.0 (M+1).

5h: 6-(4-Ethoxy-3-trifluoromethyl-phenyl)-2-[(4-N,N-dimethylcarbamoyl-piperazin-1-yl)methyl]-1H-Imidazo[4,5-c]pyridine-4-carbonitrile ¹H NMR (MeOD) δ 8.29-8.26 (m, 3H) 7.26 (d, 1H) 4.72 (s, 2H) 4,23 (q, 2H) 3.56-3.48 (m, 8H) 2.90 (s, 6H) 1.46 (t, 3H). MS m/z 502.3.

5i: 2-(3-Dimethylamino-azetidin-1-ylmethyl)-6-(4-ethoxy-3-trifluoromethyl-phenyl)-1H-Imidazo[4,5-c]pyridine-4-carbonitrile ¹H NMR (MeOD) δ 8.38-8.34 (m, 3H) 7.331 (d, 1H) 5.16 (m, 1H) 5.08 (s, 1H) 4.81 (s, 2H), 4.77 (m, 1H) 4.49 (m, 1H) 4.25 (q, 2H), 3.47 (s, 3H) 3.42 (s, 1H) 3.31 (s, 3H) 1.46 (q, 3H). MS m/z 445.5 (M+1).

5j: 6-(4-Ethoxy-3-trifluoromethyl-phenyl)-2-{[(5-methyl-isoxazol-3-ylmethyl)-amino]-methyl}-1H-imidazo[4,5,c]pyridine-4-carbonitrile ¹H NMR (MeOD) δ 8.30-8.24 (m, 3H), 7.25 (d, 1H) 6.33 (s, 1H) 4.74 (s, 2H) 4.56 (s, 2H) 4.22 (q, 2H) 2.46 (s, 3H), 1.45 (t, 3H). MS m/z 457.8 (M+1).

5k: 2-Aminomethyl-6-(4-ethoxy-3-trifluoromethyl-phenyl)-1H-imidazo[4,5,c]pyridine-4-carbonitrile ¹H NMR (MeOD) δ8.31-8.26 (m, 3H) 7.29 (d, 1H) 4.54 (s, 2H) 4.23 (q, 2H) 1.45 (t, 3H). MS m/z 362.6 (M+1).

5l: 6-(4-Ethoxy-3-trifluoromethyl-phenyl)-2-methylaminomethyl-1H-imidazo [4,5,c]-pyridine-4-carbonitrile $^1$H NMR (MeOD) δ 8.31-8.26 (m, 3H) 7.26 (d, 1H(, 4.64 (s, 2H) 4.23 (q, 2H) 2.95 (s, 3H) 1.45 (t, 3H). MS m/z 376.6 (M+1).

5m: 2-Dimethylaminomethyl-6-(4-ethoxy-3-trifluoromethyl-phenyl)-1H-imidazo [4,5,c]-pyridine-4-carbonitrile $^1$H NMR (MeOD) δ 8.31-8.25 (m, 3H) 7.28 (d, 2H) 4.23 (q, 2H) 3.14 (s, 6H) 1.46 (t, 3H). MS m/z 390.6 (M+1).

5n: (4-Ethoxy-3-trifluoromethyl-phenyl)-2-[(4-carbamoylpiperidin-1-yl)methyl]-1H-imidazo[4,5-c]pyridine-4-carbonitrile $^1$H NMR (MeOD) δ 8.29-8.24 (m, 3H) 7.25 (d, 1H) 4.76 (s, 2H) 4.22 (q, 2H) 3.84-3.81 (m, 2H) 3.35-3.30 (m, 2H) 2.64 (m, 1H) 2.16-2.07 (m, 4H) 1.45 (t, 3H). MS m/z 473.3 (M+1).

5o: 2-[(N-Allyl-N-methyl-amino)-methyl]-(4-ethoxy-3-trifluoromethyl-phenyl)-1H-imidazo[4,5-c]pyridine-4-carbonitrile $^1$H NMR (MeOD) δ 8.30-8.25 (m, 3H) 7.27 (d, 2H) 6.08 (m, 1H) 5.69 (m, 2H) 4.79 (s, 2H) 4.23 (q, 2H) 4.05 (d, 2H) 3.09 (s, 3H) 1.46 (q, 3H). MS m/z 416.8 (M+1).

5p: 2-(4-Acetyl-piperazin-1-ylmethyl)-6-(4-ethoxy-3-trifluoromethyl-phenyl)-1H-imidazo[4,5-c]pyridine-4-carbonitrile $^1$H NMR (MeOD) δ 8.28-8.23 (m, 3H) 7.26 (s, 1H) 4.65 (s, 2H) 4.23 (q, 2H) 3.88 (m, 4H) 3.44-3.30 (m, 4H) 2.16 (s, 3H) 1.46 (t, 3H). MS m/z 473.3 (M+1).

5q: 6-(4-Ethoxy-3-trifluoromethyl)-phenyl)-2-[(4-ethoxycarbonylpiperizin-1-yl)methyl]-1H-imidazo[4,5-c]pyridine-4-carbonitrile $^1$H NMR (MeOD) δ 8.26-8.20 (m 3H) 7.25 (d, 1H) 4,52 (s, 2H) 4.24-4.13 (m, 4H) 3.75 (m, 4H) 3.23 (m, 4H) 1.45 (t, 3H) 1.26 (t, 3H). MS m/z 503.0 (M+1).

5r: 6-(4-Ethoxy-3-trifluoromethyl-phenyl)-2-{[3-(2-oxo-pyrorrolidin-1-yl)-propylamino]-methyl}1H-imidazo [4,5-c]pyridine-4-carbonitrile $^1$H NMR (MeOD) δ 8.31-8.25 (m, 3H) 7.27 (d, 1H) 4.67 (s, 2H) 4.23 (q, 2H) 3.53 (t, 2H) 3.46 (t, 2H) 3.29 (m, 2H) 2.42 (t, 2H) 2.13-2.03 (m, 4H) 1.45 (t, 3H). MS m/z 487.5 (M+1).

5s: 6-(4-Ethoxy-3-trifluoromethyl-phenyl)-2-(4-pyrrolidin-1-yl-piperidin-1-yl)-1H-imidazo[4,5-c]pyridine-4-carbonitrile $^1$H NMR (MeOD) δ 8.31-8.23 (m, 3H) 7.29 (d, 1H) 4.35 (s, 2H) 4.24 (q, 2H) 3.68-3.45 (m, 6H) 3.21-3.10 (m, 2H) 2.86-2.81 (m, 2H) 2.39-1.90 (m, 7H) 1.45 (t, 3H). MS m/z 499.4 (M+1).

5t: 6-(4-Ethoxy-3-trifluoromethyl-phenyl)-2-[4-(furan-2-ylcarbonyl)-piperazin-1-ylmethyl]-1H-imidazo [4,5-c]pyridine-4-carbonitrile $^1$H NMR (MeOD) δ 8.26 (s, 1H) 8.23 (d, 1H), 8.18 (s, 1H) 7.68 (s, 1H) 7.24 (d, 1H) 7.09 (m, 1H) 6.59 (m, 1H) 4.4 (s, 2H) 4.21 (q, 2H) 4.04 (m, 4H) 3.18 (m, 4H) 1.45 (t, 3H). MS m/z 525.7 (M+1).

5u: 6-(4-Ethoxy-3-trifluoromethyl-phenyl)-2-[(2-methoxy-ethylamino)-methyl]-1H-imidazo[4,5-c]pyridine-4-carbonitrile $^1$H NMR (MeOD) δ 8.32-8.26 (m, 3H) 7.29 (d, 1H) 4.69 (s, 2H) 4.24 (q, 2H) 3.77 (m, 2H) 3.53 (m, 2H) 3.46 (s, 3H) 1.46 (t, 3H). MS m/z 420.3 (M+1).

5v: 2-(2,6-Dimethyl-piperidin-1ylmethyl)-6-(4-ethoxy-3-trifluoromethyl-phenyl)]-1H-imidazo[4,5-c]pyridine-4-carbonitrile $^1$H NMR (MeOD) δ 8.31-8.26 (m, 3H) 7.28 (d, 1H) 4.9-4.6 (m, 2H) 4.23 (q, 2H) 3.89-3.71 (m, 2H) 2.07-1.63 (m, 6H) 1.61-1.32 (m, 9H). MS m/z 459.0 (M+1.5). 5w: 6-(4-Ethoxy-3-trifluoromethyl-phenyl)-2-{[(furan-2-ylmethyl)-amino]-methyl}-1H-imidazo[4,5-c]pyridine-4-carbonitrile $^1$H NMR (MeOD) δ 8.30-8.25 (m, 3H) 7.66 (s, 1H) 7.27 (d, 1H) 6,7 (m, 1H) 6.52 (m, 1H) 4.62 (s, 2H) 4,56 (s, 2H) 4.23 (q, 2H) 1.45 (t, 3H). MS m/z 442.5 (M+1).

5x: 2-[(Cyclopropylmethyl-amino)-methyl]-6-(4-ethoxy-3-trifluoromethyl-phenyl)-1H-imidazo[4,5-c]pyridine-4-carbonitrile $^1$H NMR (MeOD) δ 8.31-8.26 (m, 3H) 7.28 (d, 1H) 4.68 (s, 2H) 3.17 (d, 2H) 1.45 (t, 3H) 1.21 (m, 1H) 0.77 (m, 2H) 0.48 (m, 2H). MS m/z 416.5 (M+1).

EXAMPLE 6a

2-[(1-Aza-bicyclo[2.2.2]oct-3-ylamino)-methyl]-6-(4-ethoxy-3-trifluoromethyl-phenyl)-1H-imidazo[4,5-c]pyridine-4-carbonitrile

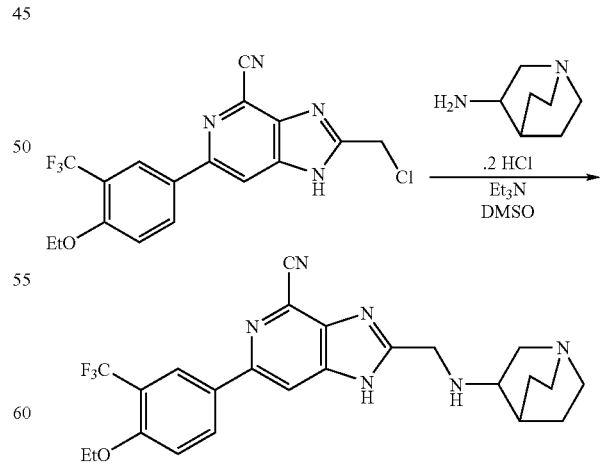

A solution of 2-chloromethyl-6-(4-ethoxy-3-trifluoromethyl-phenyl)-1H-imidazo[4,5-c]pyridine-4-carbonitrile (20 mg, 0.06 mmol), 3-aminoquinuclidine dihydrochloride (22.9 mg, 0.12 mmol) and triethylamine (18.2 mg, 0.18 mmol) in dimethylsulfoxide(500 μL) was heated in the Creator microwave at 120° C. for 5 minutes. The mixture was filtered and purified by preparative HPLC to afford 2-[(1-aza-bicyclo [2.2.2]oct-3-ylamino)-methyl]-6-(4-ethoxy-3-trifluoromethyl-phenyl)-1H-imidazo[4,5-c]pyridine-4-carbonitrile (14.8 mg) ¹H NMR (MeOD) δ 8.34-8.27 (m, 3H) 7.29 (d, 2H) 4.95 (s, 2H) 4.29-4.21 (m, 3H) 4.00 (m, 1H) 3.86-3.69 (m 5H) 2.46 (m, 1H) 2.27-2.10 (m, 4H) 1.45 (t, 3H). MS m/z 471.8 (M+1).

The procedure described in Example 6 was further applied, using the appropriate amine derivatives, to prepare the following compounds:

6b: 6-(4-Ethoxy-3-trifluoromethyl-phenyl)-2-{[(thiazol-2-ylmethyl)-amino]-methyl}-1H-imidazo[4,5-c]pyridine-4-carbonitrile ¹H NMR (MeOD) δ 8.31-8.27 (m, 3H) 7.92 (d, 1H) 7.75 (d, 1H) 7.28 (d, 1H) 4.89 (s, 2H) 4.23 (q, 2H) 1.46 (t, 3H). MS m/z 459.6 (M+1).

6c: 6-(4-Ethoxy-3-trifluoromethyl-phenyl)-2-(carbamoylmethylaminomethyl)-1H-imidazo[4,5-c]pyridine-4-carbonitrile ¹H NMR (MeOD) δ 8.31-8.25 (m, 3H) 7.28 (d, 1H) 4.18 (bs, 2H) 4.23 (q, 2H) 4.07 (bs, 2H) 1.45 (t, 3H). MS m/z 419.4 (M+1).

6d: 6-(4-Ethoxy-3-trifluoromethyl-phenyl)-2-(pyridin-4-ylaminomethyl)-1H-imidazo[4,5-c]pyridine-4-carbonitrile ¹H NMR (MeOD) δ 8.28-8.22 (m, 5H) 7.27 (d, 1H) 6.93 (m, 2H) 5.75 (s, 2H) 4.23 (q, 2H) 1.45 (t, 3H). MS m/z 439.5 (M+1).

EXAMPLE 7

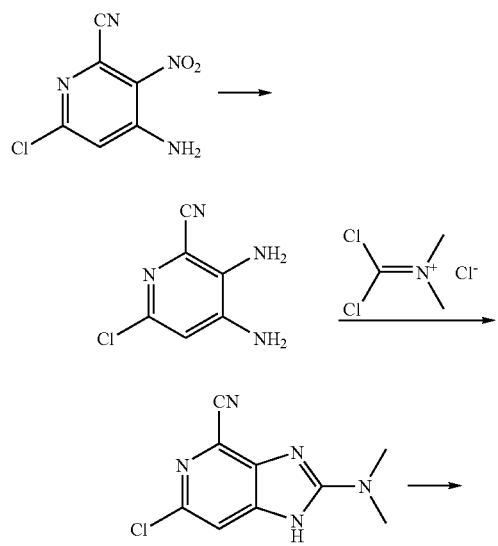

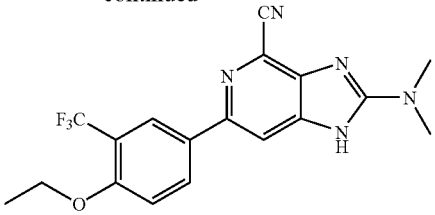

A: 6-Chloro-2-dimethylamino-1H-imidazo[4,5-c]pyridine-4-carbonitrile

Iron powder (8.5 g) was added in small portions to a solution of 4-amino-6-chloro-2-cyano-3-nitropyridine in MeOH (90 ml) and concentrated hydrochloric acid (30 ml) during 20 minutes. The mixture was refluxed for another 30 minutes. After cooling, the reaction mixture was basified with concentrated aqueous ammonia to pH 10. The mixture was extracted with ethyl acetate (200 ml×5), combined organic layer was washed with brain, dried over sodium sulphate, solvent removed under vacuum to give crude product (4 g) which is used for next step without further purification. The above crude product (0.33 g) was added to chloroform (5 ml) and acetonitrile (20 ml) and followed by dichloromethylene dimethylammonium chloride(0.33 g). The mixture was refluxed for 4hours. After cooling, solid product, 6-chloro-2-dimethylamino-1H-imidazo[4,5-c]pyridine-4-carbonitrile was collected by filtration. ¹H NMR (MeOD) δ 7.61(s, 1H), 3.37(s, 3H), 3.30(s, 3H).

B: 2-Dimethylamino-6-(4-ethoxy-3-trifluoromethyl-phenyl)-1H-imidazo[4,5-c]pyridine-4-carbonitrile A suspension of 6-chloro-2-dimethylamino-1H-imidazo [4,5-c]pyridine-4-carbonitrile (100 mg, 0.45 mmol), 4-ethoxy-3-trifluoromethyl-phenyl boronic acid (198 mg, 0.88 mmol) tetrakis(triphenylphosphine)palladium(0) (50 mg, ~10 mol %) and potassium carbonate (193.0 mg, 1.39 mmol) in THF (3 ml) was heated to 130° C. for 6 minutes in the "Smith" microwave. The crude mixture was concentrated under reduced pressure to remove THF before partitioning between ethyl acetate and water. The organic layer was separated, dried over sodium sulfate and concentrated under reduced pressure. The material was then dissolved in DMSO and purified in aliquots by preparative HPLC. The desired fractions were collected and concentrated to give a white solid which was washed with ether to afford 2-dimethylamino-6-(4-ethoxy-3-trifluoromethyl-phenyl)-1H-imidazo [4,5-c]pyridine-4-carbonitrile (5.0 mg)

¹H NMR (DMSO) δ 8.24 (m, 2H) 7.84 (s, 1H) 7.35 (d, 1H) 4.24 (q, 2H) 3.19 (s, 6H), 1.37 (t, 3H). MS m/z 376.7 (M+1).

EXAMPLE 8

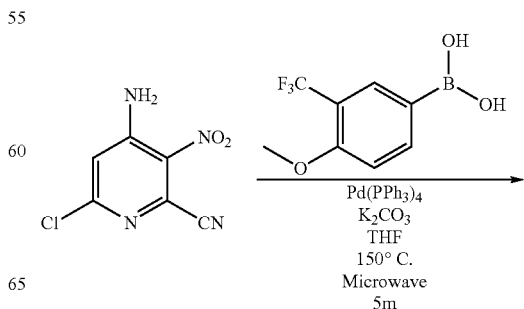

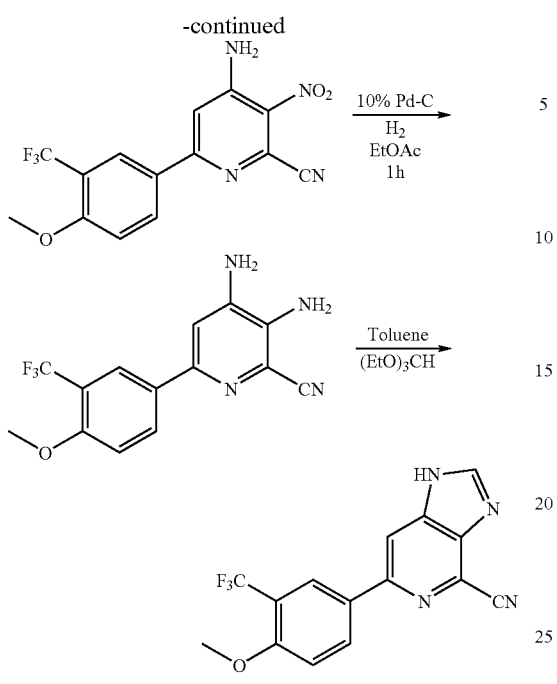

A: 4-Amino-6-(4-methoxy-3-trifluoromethyl-phenyl)-3-nitro-pyridine-2-carbonitrile A stirred mixture 4-amino-6-chloro-3-nitro-pyridine-2-carbonitrile (152 mg, 0.76 mmol), 4-methoxy-3-trifluoromethylphenylboronic acid (332 mg,1.51 mmol), tetrakis(triphenylphosphine)palladium(0) (115 mg, 10 mol %), potassium carbonate (418 mg, 3.03 mmol) and THF (5 ml) was degassed under a stream of nitrogen before heating in the Smith Creator microwave at 150° C. for 10 minutes. The crude mixture was concentrated under reduced pressure to remove THF before partitioning between ethyl acetate (20 ml) and water (20 ml). The organic layer was separated, dried over sodium sulfate and concentrated under reduced pressure to give a dark brown oil. Mixture was flash chromatographed over silica (10 g Combiflash cartridge, 7:3 heptane/ethyl acetate to 1:1 heptane/ethyl acetate) to afford 68 mg of 4-amino-6-(4-methoxy-3-trifluoromethyl-phenyl)-3-nitro-pyridine-2-carbonitrile as an orange solid. $^1$H NMR (DMSO) δ 8.25 (d, 1H), 8.18 (m, 2H), 7.62 (s, 2H), 7.46 (d, 1H), 3.99 (s, 3H). MS m/z 339.3 (M+1).

B: 3,4-Diamino-6-(4-methoxy-3-trifluoromethyl-phenyl)-pyridine-2-carbonitrile

4-Amino-6-(4-methoxy-3-trifluoromethyl-phenyl)-3-nitro-pyridine-2-carbonitrile (65 mg, 0.19 mmol) was suspended in methanol (1.5 ml) and concentrated HCl (0.5 ml) was added dropwise (exotherm). The suspension was stirred while iron powder (37 mg, 0.67 mmol) was added in portions (exotherm), and the mixture was heated to reflux for 1 hour. Mixture was poured into water (20 ml) and extracted with ethyl acetate (20 ml). Organics were dried and evaporated then flash chromatographed over silica (4 g Combiflash cartridge, 7:3 heptane/ethyl acetate) to afford 29 mg of 3,4-diamino-6-(4-methoxy-3-trifluoromethyl-phenyl)-pyridine-2-carbonitrile as a light brown solid. $^1$H NMR (DMSO) δ 8.08-8.01 (m, 2H) 7.05-7.00 (m, 2H), 3.94 (s, 3H). MS m/z 309.7 (M+1).

C: 6-(4-Methoxy-3-trifluoromethyl-phenyl)-1H-imidazo[4,5-c]pyridine-4-carbonitrile 3,4-Diamino-6-(4-methoxy-3-trifluoromethyl-phenyl)-pyridine-2-carbonitrile (20 mg, 0.065 mmol) was suspended in toluene (1 ml), triethylorthoformate (12 mg, 0.078 mmol) was added in one portion and the mixture was heated to reflux overnight. Mixture was prep-LCMS purified to afford 7 mg of 6-(4-methoxy-3-trifluoro-methyl-phenyl)-1H-imidazo[4,5-c]pyridine-4-carbonitrile as a white solid. $^1$H NMR (DMSO) δ 8.68 (s, 1H), 8.45-8.35 (m, 2H), 8.31 (s, 1H), 7.40 (d, 1H), 3.98 (s, 3H). MS m/z 319.1 (M+1).

EXAMPLE 9a 6-(4-Ethoxy-3-trifluoromethyl-phenyl)-1-(2-morpholin-4-yl-ethyl)-1H-imidazo[4,5-c]pyridine-4-carbonitrile

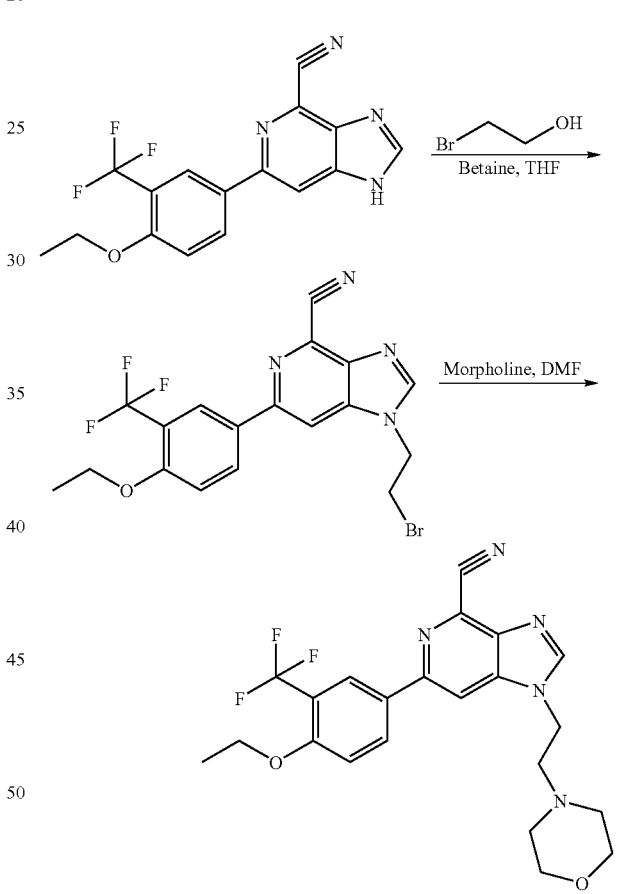

A: 1-(2-Bromo-ethyl)-6-(4-ethoxy-3-trifluoromethyl-phenyl)-1H-imidazo[4,5-c]pyridine-4-carbonitrile 6-(4-Ethoxy-3-trifluoromethyl-phenyl)-1H-imidazo[4,5-c]pyridine-4-carbonitrile (300 mg, 0.90 mmol) was dissolved in THF (10 ml), 2-bromoethanol was added (225 mg, 1.80 mmol) followed by betaine (738 mg, 1.80 mmol), and the mixture was stirred at room temperature for 3 hours. A further 0.5 equivalents of betaine (0.45 mmol, 162 mg) was added and the mixture was stirred at room temperature for a further hour. Mixture was partitioned between ethyl acetate (20 ml) and water (20 ml). Organics were dried and evaporated then flash chromatographed over silica (10 g Combiflash cartridge, DCM to 1% methanol in DCM) to afford a white solid which was mixture of N-1 and N-3 alkylated products. Mixture was flash chromatographed over silica (10 g Flashmaster cartridge, toluene to 20% ethyl acetate in toluene) to afford 130 mg of 1-(2-bromo-ethyl)-6-(4-ethoxy-3-trifluoromethyl-phenyl)-1H-imidazo[4,5-c]pyridine-4-carbonitrile as a white solid. $^1$H NMR (DMSO) δ 8.80 (s, 1H), 8.74 (s, 1H), 8.48-8.39 (m, 2H), 7.44 (d, 1H), 4.88 (t, 2H), 4.29 (q, 2H), 4.05 (t, 2H), 1.40 (t, 3H).

B: 6-(4-Ethoxy-3-trifluoromethyl-phenyl)-1-(2-morpholin-4-yl-ethyl)-1H-imidazo[4,5-c]pyridine-4-carbonitrile 1-(2-Bromo-ethyl)-6-(4-ethoxy-3-trifluoromethyl-phenyl)-1H-imidazo[4,5-c]pyridine-4-carbonitrile (92 mg, 0.21 mmol) was dissolved in DMF (2 ml) and morpholine (91 mg, 1.05 mmol) was added. The mixture was heated to 120° C. for 5 minutes in a Smith microwave. Mixture was diluted with methanol (5 ml) and passed through a 5 g SCX cartridge then eluted with 2M methanolic ammonia to afford 62 mg of 6-(4-ethoxy-3-trifluoromethyl-phenyl)-1-(2-morpholin-4-yl-ethyl)-1H-imidazo[4,5-c]pyridine-4-carbonitrile as a clear oil. $^1$H NMR (CDCl$_3$) δ 8.26-8.15 (m, 3H), 7.87 (s, 1H), 7.08 (d, 1H), 4.35 (t, 2H), 4.20 (q, 2H), 3.69 (m, 4H), 2.82 (t, 2H), 2.52 (m, 4H), 1.48 (t, 3H). MS m/z 446.4 (M+1).

The procedure described in Examples 9 above was further applied, using the appropriate amine derivatives, to prepare the following compounds:

9b: 1-[2-(Cycloprorylmethyl-amino)-ethyl]-6-(4-ethoxy-3-trifluoromethyl-phenyl)-1H-imidazo[4,5-c]pyridine-4-carbonitrile $^1$H NMR (CDCl$_3$) δ 8.23 (m, 2H), 8.18 (s, 1H), 7.92 (s, 1H), 7.11 (d, 1H), 4.35 (t, 2H), 4.20 (q, 2H), 3.14 (t, 2H), 2.50 (d, 2H), 1.48 (t, 3H), 0.88 (m, 1H), 0.48 (m, 2H), 0.08 (m, 2H). MS m/z 430.5 (M+1).

9c: 6-(4-Ethoxy-3-trifluoromethyl-phenyl)-1-(2-ethylamino-ethyl)-1H-imidazo[4,5-c]-pyridine-4-carbonitrile $^1$H NMR (CDCl$_3$) δ 8.29-8.18 (m, 3H), 7.92 (s, 1H), 7.12 (d, 1H), 4.35 (t, 2H), 4.20 (q, 2H), 3.12 (t, 2H), 2,67 (q, 2H), 1.49 (t, 3H), 1.08 (t, 3H). MS m/z 404.7 (M+1).

9d: 6-(4-Ethoxy-3-trifluoromethyl-phenyl)-1-(2-piperidin-1-yl-ethyl)-1H-imidazo[4,5-c]-pyridine-4-carbonitrile $^1$H NMR (CDCl$_3$) δ 8.28-8.22 (m, 2H), 8.19 (s, 1H), 7.92 (s, 1H), 7.12 (d, 1H), 4.32 (t, 2H), 4.22 (q, 2H), 2.74 (t, 2H), 2.45 (m, 4H), 1.59-1.43 (m, 9H). MS m/z 444.5 (M+1).

9e: 6-(4-Ethoxy-3-trifluoromethyl-phenyl)-1-(2-pyrolidin-1-yl-ethyl)-1H-imidazo[4,5-c]-pyridine-4-carbonitrile, trifluoro-acetic acid salt $^1$H NMR (MeOH) δ 8.57 (s, 1H), 8.51 (s, 1H), 8.39 (m, 2H), 7.30 (d, 1H), 4.88 (m, 2H), 4.24 (q, 2H), 3.86 (t, 2H), 3.79-3.58 (m, 2H), 3.24 (m, 2H), 2.35-1.95 (m, 4H), 1.46 (t, 3H). MS m/z 430.5 (M+1).

9f: 1-(2-Dimethylamino-ethyl)-6-(4-ethoxy-3-trifluoromethyl-phenyl)-1H-imidazo [4,5-c]pyridine-4-carbonitrile $^1$H NMR (CDCl$_3$) δ 8.26-8.23 (m, 2H), 8.18 (s, 1H), 7.88 (s, 1H), 7.11 (d, 1H), 4.31 (t, 2H), 4.21 (q, 2H), 2.75 (t, 2H), 2.31 (s, 6H), 1.49 (t, 3H). MS m/z 404.7 (M+1).

9g: 1-[2-(2-Dimethylamino-ethylamino)-ethyl]-6-(4-ethoxy-3-trifluoromethyl-phenyl)-1H-imidazo[4,5-c]pyridine-4-carbonitrile $^1$H NMR (MeOH) δ 8.97 (m, 1H), 8.78 (m, 1H), 8.43 (m, 2H), 7.29 (d, 1H), 4.99 (m, 2H), 4.23 (q, 2H), 3.79 (m, 2H), 3.60 (m, 4H), 2.96 (s, 6H), 1.45 (t, 3H). MS m/z 447.4 (M+1).

EXAMPLE 10a 6-(4-Ethoxy-3-trifluoromethyl-phenyl)-1-(3-morpholin-4-yl-propyl)-1H-imidazo[4,5-c]pyridine-4-carbonitrile

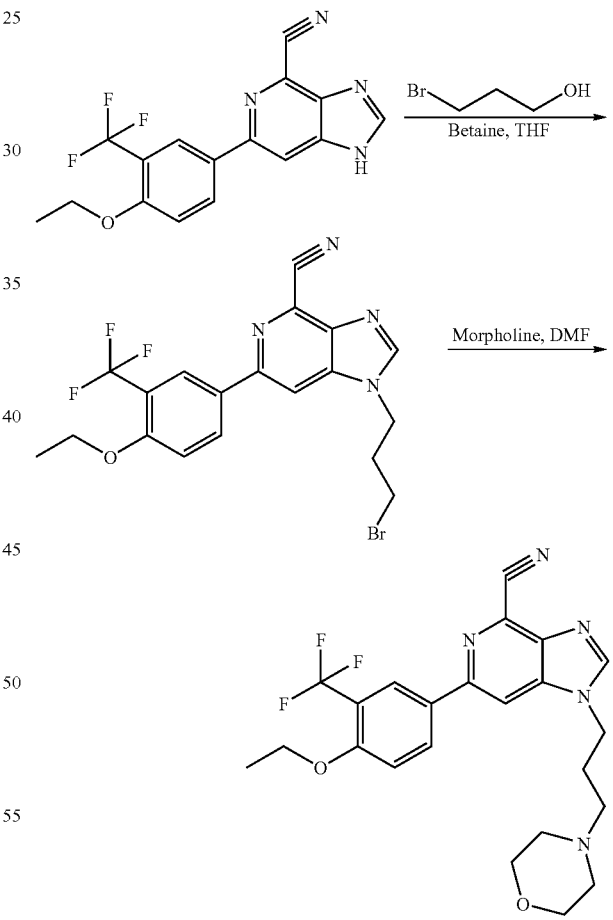

A: 1-(3-Bromo-propyl)-6-(4-ethoxy-3-trifluoromethyl-phenyl)-1H-imidazo[4,5-c]-pyridine-4-carbonitrile 6-(4-Ethoxy-3-trifluoromethyl-phenyl)-1H-imidazo[4,5-c]pyridine-4-carbonitrile (500 mg, 1.51 mmol) was dissolved in THF (20 ml), 3-bromopropanol was added (396 mg, 3.0 mmol) followed by betaine (1.23 g, 2.0 mmol), and the mixture was stirred at room temperature for 2 hours. A further 0.5 equivalents of betaine (0.45 mmol, 162 mg) was added and the mixture was stirred at room temperature for a further 16 hours. Mixture was partitioned between ethyl acetate (100 ml) and water (100 ml). Organics were dried and evaporated then flash chromatographed over silica (40 g Combiflash cartridge, toluene to 40% ethyl acetate in toluene) to afford 520 mg of a white solid. Mixture was triturated with ether then resulting solid was washed with ether (20 ml) to afford 310 mg of 1-(3-bromo-propyl)-6-(4-ethoxy-3-trifluoromethyl-phenyl)-1H-imidazo[4,5-c]pyridine-4-carbonitrile as a white solid. $^1$H NMR (DMSO) δ 8.30-8.22 (m, 2H), 8.18 (s, 1H), 7.98 (s, 1H), 7.13 (d, 1H), 4,56 (t, 2H), 4.23 (q, 2H), 3.48 (t, 2H), 2.48 (m, 2H), 1.50 (t, 3H).

B: 6-(4-Ethoxy-3-trifluoromethyl-phenyl)-1-(3-morpholin-4-yl-propyl)-1H-imidazo[4,5-c]pyridine-4-carbonitrile 1-(3-Bromo-propyl)-6-(4-ethoxy-3-trifluoromethyl-phenyl)-1H-imidazo[4,5-c]pyridine-4-carbonitrile was dissolved in DMF (0.5 ml) and morpholine (19 mg, 0.22 mmol) was added. The mixture was heated to 120° C. in a Smith Creator microwave. Mixture was diluted with methanol and passed through an SCX cartridge, then eluted with 2M methanolic ammonia. Mixture was then prep HPLC purified and acetonitrile was removed under reduced pressure. Resulting aqueous solution was made basic with sodium bicarbonate, extracted into DCM (5 ml), then organics were dried and evaporated to afford 6-(4-ethoxy-3-trifluoromethyl-phenyl)-1-(3-morpholin-4-yl-propyl)-1H-imidazo[4,5-c]pyridine-4-carbonitrile as a white solid (8 mg). $^1$H NMR (CDCl$_3$) δ 8.25 (d, 1H), 8.18 (s, 1H), 8.14 (s, 1H), 7.89 (s, 1H), 7.11 (d, 1H), 4.42 (t, 2H), 4.21 (q, 2H), 3.71 (m, 4H), 2.37 (m, 4H), 2.26 (t, 2H), 2.08 (m, 2H), 1.49 (t, 3H). MS m/z 460.6 (M+1).

The procedure described in Example 10 above was further applied, using the appropriate amine derivatives, to prepare the following compounds:

10b: 6-(4-Ethoxy-3-trifluoromethyl-phenyl)-1-(3-ethylamino-propyl)-1H-imidazo[4,5-c]pyridine-4-carbonitrile $^1$H NMR (CDCl$_3$) δ 8.27 (d, 1H), 8.20 (s, 1H), 8.14 (s, 1H), 7.97 (s, 1H), 7.12 (d, 1H), 4.45 (t, 2H), 4.21 (q, 2H), 2,61 (m, 4H), 2.06 (m, 2H), 1.50 (t, 3H), 1.10 (t, 3H). MS m/z 404.7 (M+1).

10c: 1-[3-(Cyclopropylmethyl-amino)-propyl]-6-(4-ethoxy-3-trifluoromethyl-phenyl)-1H-imidazo[4,5-c]pyridine-4-carbonitrile $^1$H NMR (CDCl$_3$) δ 8.27 (d, 1H), 8.20 (s, 1H), 8.15 (s, 1H), 7.97 (s, 1H), 7.13 (d, 1H), 4.46 (t, 2H), 4.21 (q, 2H), 2,61 (t, 2H), 2.42 (d, 2H), 2.07 (m, 2H), 1.49 (t, 3H), 0.91 (m, 1H), 0.48 (m, 2H), 0.10 (m, 2H). MS m/z 444.8 (M+1).

10d: 6-(4-Ethoxy-3-trifluoromethyl-phenyl)-1-(3-piperidin-1-yl-propyl)-1H-imidazo[4,5-c]pyridine-4-carbonitrile $^1$H NMR (CDCl$_3$) δ 8.26 (d, 1H), 8.20 (s, 1H), 8.15 (s, 1H), 7.92 (s, 1H), 7.12 (d, 1H), 4.40 (t, 2H), 4.21 (q, 2H), 2.37-2.25 (m, 4H), 2.20 (t, 2H), 2.05 (m, 2H), 1.67-1.40 (m, 9H). MS m/z 459.0 (M+1).

10e: 6-(4-Ethoxy-3-trifluoromethyl-phenyl)-1-(3-pyrrolidin-1-yl-propyl)-1H-imidazo[4,5-c]pyridine-4-carbonitrile $^1$H NMR (CDCl$_3$) δ 8.36 (d, 1H), 8.20 (s, 1H), 8.13 (s, 1H), 7.97 (s, 1H), 7.12 (d, 1H), 4.43 (t, 2H), 4.21 (q, 2H), 2.45 (m, 4H), 2.38 (t, 2H), 2.08 (m, 2H), 1.80 (m, 4H), 1.49 (t, 3H). MS m/z 444.8 (M+1).

10f: 1-(3-Dimethylamino-propyl)-6-(4-ethoxy-3-trifluoromethyl-phenyl)-1H-imidazo-[4,5-c]pyridine-4-carbonitrile $^1$H NMR (CDCl$_3$) δ 8.29 (d, 1H), 8.21 (s, 1H), 8.14 (s, 1H), 7.97 (s, 1H), 7.12 (d, 1H), 4.41 (t, 2H), 4.32 (q, 2H), 2.26-2.16 (m, 8H), 2.05 (m, 2H), 1.49 (t, 3H). MS m/z 418.6 (M+1).

10g: 1-(3-tert-Butylamino-propyl)-6-(4-ethoxy-3-trifluoromethyl-phenyl)-1H-imidazo-[4,5-c]pyridine-4-carbonitrile; compound as trifluoro-acetic acid salt $^1$H NMR (MeOH) δ 8.53 (s, 1H), 8.43 (s, 1H), 8.36 (m 2H), 7.30 (d, 1H), 4,57 (t, 2H), 4.26 (q, 2H), 3.11 (m, 2H), 2.30 (m, 2H), 1.48 (t, 3H), 1.37 (s, 9H). MS m/z 446.4 (M+1).

EXAMPLE 11a 6-(4-Ethoxy-3-trifluoromethyl-phenyl)-2-(4-methyl-piperazin-1-ylmethyl)-1H-imidazo-[4,5-c]pyridine-4-carbonitrile

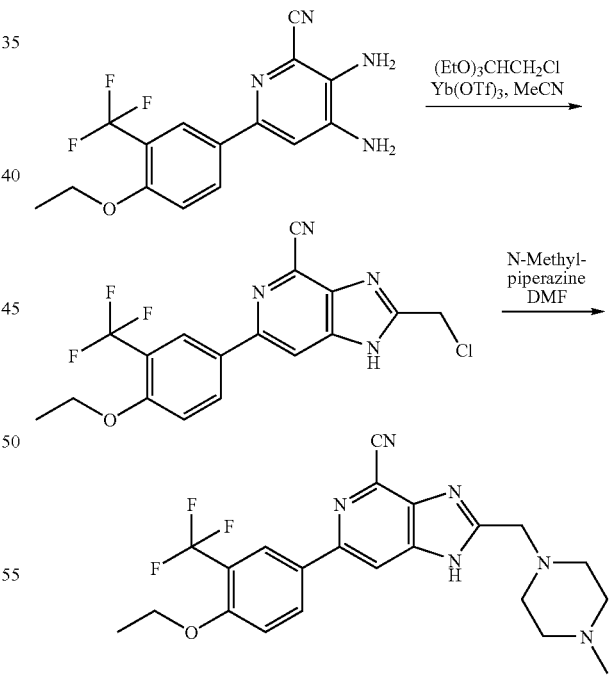

A: 2-Chloromethyl-6-(4-ethoxy-3-trifluoromethyl-phenyl)-1H-imidazo[4,5-c]pyridine-4-carbonitrile 3,4-Diamino-6-(4-ethoxy-3-trifluoromethyl-phenyl)-pyridine-2-carbonitrile (1 g, 3.1 mmol) was dissolved in acetonitrile (20 ml) and ytterbium triflate (38 mg, 0.062 mmol) and 2-chloro-1,1,1-triethoxyethane (1.83 g, 9.3 mmol) were added. The mixture was heated to reflux overnight. Mixture was evaporated under reduced pressure, partitioned between ethyl acetate (100 ml) and water (100 ml), and organics were dried then evaporated under reduced pressure to afford a dark brown oil. Triturated with DCM (50 ml) to afford 495 mg of 2-chloromethyl-6-(4-ethoxy-3-trifluoromethyl-phenyl)-1H-imidazo[4,5-c]pyridine-4-carbonitrile as a light brown solid. $^1$H NMR (DMSO) δ 8.47-8.33 (m, 3H), 7.41 (d, 1H), 5.05 (s, 2H), 4.26 (q, 2H), 1.38 (t, 3H). MS m/z 381.1 (M+1).

B: 6-(4-Ethoxy-3-trifluoromethyl-phenyl)-2-(4-methyl-piperazin-1-ylmethyl)-1H-imidazo[4,5-c]pyridine-4-carbonitrile 2-Chloromethyl-6-(4-ethoxy-3-trifluoromethyl-phenyl)-1H-imidazo[4,5-c]pyridine-4-carbonitrile (20 mg, 0.053 mmol) was dissolved in DMF and N-methyl piperazine (26 mg, 0.26 mmol) was added. The mixture was heated to 120° C. for five minutes in a Smith Creator microwave. Mixture was diluted with methanol (4 ml) and loaded onto an SCX cartridge. Cartridge was washed three times with methanol (5 ml) then eluted with 2M methanolic ammonia. Methanolic ammonia was removed by evaporation under reduced pressure then mixture was prep HPLC purified to afford 8 mg of 6-(4-ethoxy-3-trifluoromethyl-phenyl)-2-(4-methyl-piperazin-1-ylmethyl)-1H-imidazo[4,5-c]pyridine-4-carbonitrile as a white solid. $^1$H NMR (MeOH) δ 8.28-8.20 (m, 2H), 8.13 (s, 1H), 7.26 (d, 1H), 4.22 (q, 2H), 3.92 (s, 2H), 2,67 (m, 8H), 2.38 (s, 3H), 1.45 (t, 3H). MS m/z 445.5 (M+1).

The procedure described in Example 11 above was further applied, using the appropriate amine derivatives, to prepare the following compounds:

11b: 2-Cyclohexylaminomethyl-6-(4-ethoxy-3-trifluoromethyl-phenyl)-1H-imidazo-[4,5-c]pyridine-4-carbonitrile $^1$H NMR (MeOH) δ 8.31-8.26 (m, 3H), 7.28 (d, 1H), 4.66 (s, 2H), 4.23 (q, 2H), 3.35 (m, 1H), 2.25-2.22 (m, 2H), 1.95-1.92 (m, 2H), 1.75 (m, 1H), 1.53-1.26 (m, 8H). MS m/z 444,5 (M+1).

11c: 6-(4-Ethoxy-3-trifluoromethyl-phenyl)-2-[(2,2,2-trifluoro-ethylamino)-methyl]-1H-imidazo[4,5-c]pyridine-4-carbonitrile $^1$H NMR (MeOH) δ 8.27-8.22 (m, 2H), 8.15 (s, 1H), 7.26 (d, 1H), 4.30 (s, 2H), 4.22 (q, 2H), 3.47 (q, 2H), 1.45 (t, 3H). MS m/z 444.4 (M+1).

11d: 6-(4-Ethoxy-3-trifluoromethyl-phenyl)-2-[(3-phenyl-propylamino)-methyl]-1H-imidazo[4,5-c]pyridine-4-carbonitrile $^1$H NMR (MeOH) δ 8.31-8.26 (m, 3H), 7.32-7.14 (m, 6H), 4.64 (s, 2H), 4.23 (q, 2H), 3.26 (m, 2H), 2.78 (t, 2H), 2.14 (m, 2H), 1.45 (t, 3H). MS m/z 480.3 (M+1).

11e: 6-(4-Ethoxy-3-trifluoromethyl-phenyl)-2-[1,4]oxazepan-4-ylmethyl-1H-imidazo[4,5-c]pyridine-4-carbonitrile $^1$H NMR (MeOH) δ 8.31-8.24 (m, 3H), 7.27 (d, 1H), 4.88 (s, 2H), 4.23 (q, 2H), 3.99 (m, 2H), 3.87 (m, 2H), 3.77-3.69 (m, 4H), 2.26 (m, 2H), 1.45 (t, 3H). MS m/z 446.4 (M+1).

11f: 2-(Benzylamino-methyl)-6-(4-ethoxy-3-trifluoromethyl-phenyl)-1H-imidazo[4,5-c]pyridine-4-carbonitrile $^1$H NMR (MeOH) δ 8.31-8.25 (m, 3H), 7.59-7.49 (m, 5H), 7.28 (d, 1H), 4.64 (s, 2H), 4.49 (s, 2H), 4.23 (q, 2H), 1.45 (t, 3H). MS m/z 452.1 (M+1).

11g: 6-(4-Ethoxy-3-trifluoromethyl-phenyl)-2-(phenethylamino-methyl)-1H-imidazo-[4,5-c]pyridine-4-carbonitrile $^1$H NMR (MeOH) δ 8.33-8.25 (m, 3H), 7.40-7.26 (m, 6H), 4.69 (s, 2H), 4.23 (q, 2H), 3.54 (t, 2H), 3.14 (t, 2H), 1.45 (t, 3H). MS m/z 466.3 (M+1).

11h: 6-(4-Ethoxy-3-trifluoromethyl-phenyl)-2-[(2-hydroxy-ethylamino)-methyl]-1H-imidazo[4,5-c]pyridine-4-carbonitrile $^1$H NMR (MeOH) δ 8.32-8.27 (m, 3H), 7.29 (d, 1H), 4.70 (s, 2H), 4.23 (q, 2H), 3.92 (m, 2H), 3.41 (m, 2H), 1.45 (t, 3H). MS m/z 406.5 (M+1).

11i: 6-(4-Ethoxy-3-trifluoromethyl-phenyl)-2-(2-amino-1,1-dimethyl-2-oxo-ethylamino-methyl)-1H-imidazo[4,5-c]pyridine-4-carbonitrile $^1$H NMR (MeOH) δ 8.32-8.28 (m, 3H), 7.29 (d, 1H), 4.63 (s, 2H), 4.23 (q, 2H), 1.75 (s, 6H), 1.45 (t, 3H). MS m/z 447.3 (M+1).

10j: 2-Cyclopropylaminomethyl-6-(4-ethoxy-3-trifluoromethyl-phenyl)-1H-imidazo-[4,5-c]pyridine-4-carbonitrile $^1$H NMR (MeOH) δ 8.30-8.25 (m, 3H), 7.27 (d, 1H), 4.73 (s, 2H), 4.23 (q, 2H), 3.00 (m, 1H), 1.45 (t, 3H), 0.98 (m, 4H). MS m/z 402.4 (M+1).

11k: 2-(tert-Butylamino-methyl)-6-(4-ethoxy-3-trifluoromethyl-phenyl)-1H-imidazo-[4,5-c]pyridine-4-carbonitrile $^1$H NMR (MeOH) δ 8.28-8.20 (m, 2H), 8.13 (s, 1H), 7.27 (d, 1H), 4.22 (m, 4H), 1.45 (t, 3H), 1.30 (s, 9H). MS m/z 418.4 (M+1).

11l: 6-(4-Ethoxy-3-trifluoromethyl-phenyl)-2-morpholin-4-ylmethyl-1H-imidazo[4,5-c]-pyridine-4-carbonitrile $^1$H NMR (CDCl$_3$) δ 8.20 (m, 2H), 8.00 (bs, 1H), 7.10 (d, 1H), 4.21 (q, 2H), 3.99 (s, 2H), 3.81 (m, 4H), 2,68 (m, 4H), 1.48 (t, 3H). MS m/z 432.4 (M+1).

11m: 6-(4-Ethoxy-3-trifluoromethyl-phenyl)-2-(4-phenyl-piperazin-1-ylmethyl)-1H-imidazo[4,5-c]pyridine-4-carbonitrile $^1$H NMR (MeOH) δ 8.31-8.24 (m, 3H), 7.33-7.26 (m, 3H), 7.08 (d, 2H), 6.97 (m, 1H), 4.80 (s, 2H), 4.23 (q, 2H), 3.67 (m, 4H), 3.55 (m, 4H), 1.45 (t, 3H). MS m/z 507.3 (M+1).

11n: 6-(4-Ethoxy-3-trifluoromethyl-phenyl)-2-{[(pyridin-2-ylmethyl)-amino]-methyl}-1H-imidazo[4,5-c]pyridine-4-carbonitrile ¹H NMR (MeOH) δ 8.68 (d, 1H), 8.31-8.24 (m, 3H), 7.92 (t, 1H), 7.53 (dd, 1H), 7.46 (m, 1H), 7.28 (d, 1H), 4.76 (s, 2H), 4.65 (s, 2H), 4.23 (m, 2H), 1.45 (t, 3H). MS m/z 453.3 (M+1).

11o: 2-[(2-Dimethylamino-ethylamino)-methyl]-6-(4-ethoxy-3-trifluoromethyl-phenyl)-1H-imidazo[4,5-c]pyridine-4-carbonitrile ¹H NMR (MeOH) δ 8.33-8.25 (m, 2H), 8.22 (s, 1H), 7.28 (d, 1H), 4.38 (s, 2H), 4.23 (q, 2H), 3.37 (m, 2H), 3.31 (m, 2H), 3.02 (s, 6H), 1.45 (t, 3H). MS m/z 433.5 (M+1).

11p: 6-(4-Ethoxy-3-trifluoromethyl-phenyl)-2-(4-pyridin-4-yl-piperazin-1-ylmethyl)-1H-imidazo[4,5-c]pyridine-4-carbonitrile ¹H NMR (MeOH) δ 8.32-8.24 (m, 2H), 8.20 (s, 1H), 8.16 (d, 2H), 7.28 (d, 1H), 7.20 (d, 2H), 4.27-4.20 (m, 4H), 3.92-3.86 (m, 4H), 3.02 (m, 4H), 1.45 (t, 3H). MS m/z 508.4 (M+1).

11q: 6-(4-Ethoxy-3-trifluoromethyl-phenyl)-2-[(2-pyridin-2-yl-ethylamino)-methyl]-1H-imidazo[4,5-c]pyridine-4-carbonitrile ¹H NMR (MeOH) δ 8.84 (m, 2H), 8.31-8.25 (m, 3H), 8.12 (m, 2H), 7.28 (d, 1H), 4.77 (s, 2H), 4.24 (q, 2H), 3.80 (t, 2H), 3.50 (t, 2H), 1.45 (t, 3H). MS m/z 467.4 (M+1).

EXAMPLE 12

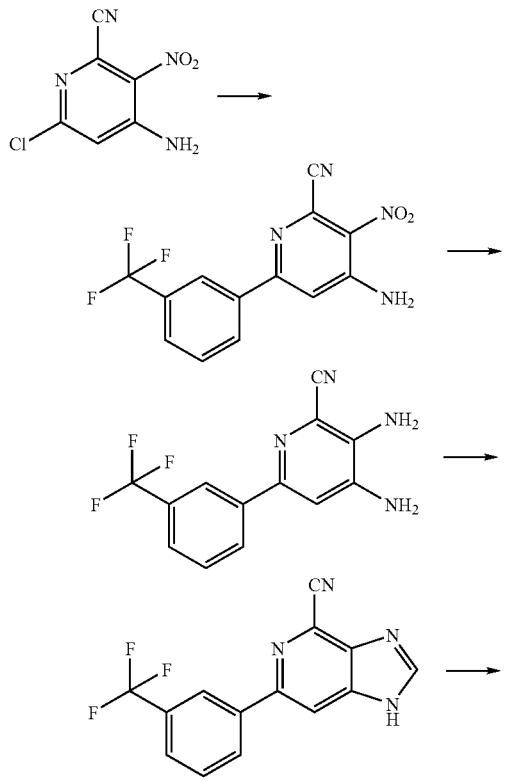

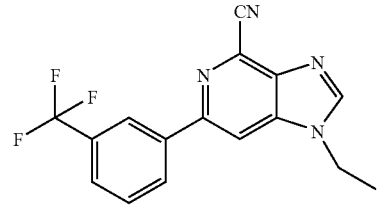

A: 4-Amino-3-nitro-6-(3-(trifluoromethyl)phenyl)-pyridine-2-carbonitril

A stirring suspension of 4-amino-6-chloro-3-nitro-pyridine-2-carbonitrile (1.0 g, 5.04 mmol), 3-(trifluoromethyl) phenyl boronic acid (1148 mg, 6.04 mmol) and potassium carbonate (2.08 g, 15.1 mmol) in THF (16 ml) was degassed with nitrogen before the addition of palladium tetrakistriphenylphosphine (582 mg, 0.50 mmol). The resulting suspension was heated to 150° C. for 5 minutes using the 'Creator' microwave. The reaction mixture was filtered through celite and concentrated in vacuo. The residual brown oil was columned on silica gel using dichloromethane as eluant to give the title compound as a yellow solid (300 mg).
¹H NMR (MeOD): δ 8.32 (s, 1H), 8.27 (d, 1H), 7.81 (d, 1H), 7.72 (t, 1H), 7.63 (s, 1H).

B: 3,4-Diamino-6-(3-(trifluoromethyl)phenyl)-pyridine-2-carbonitril

To a stirring suspension of 4-amino-3-nitro-6-(3-trifluoromethyl-phenyl)-pyridine-2-carbonitrile (300 mg, 0.97 mmol) in ethyl acetate (80 ml) was added 10% palladium on carbon (wet) (300 mg, 2.82 mmol). The vessel was purged with hydrogen (balloon) and stirred at room temperature for 1.5 hrs. Reaction mixture was filtered through celite and concentrated in vacuo to give the title compound as a dark orange solid (240 mg, 89%). 1H NMR (MeOD): δ 8.15 (s, 1H), 8.04 (d, 1H), 7.58-7.65 (m, 2H), 7.18 (s, 1H). MS m/z 279.3 (M+1).

C: 6-(3-trifluoromethyl-phenyl)-1H-imidazo[4,5-c]pyridine-4-carbonitrile:

3,4-Diamino-6-(3-trifluoromethyl-phenyl)-pyridine-2-carbonitrile (120 mg, 0.43 mmol) was suspended in acetonitrile (5 ml) and the vessel was purged with nitrogen. Ytterbium triflate (5 mg, 0.009 mmol) and triethyl orthoformate (214 µl, 1.29 mmol) were added and the resulting orange suspension was heated at reflux for 1 hour. Reaction mixture was concentrated in vacuo to give the title compound as a yellow solid (116 mg). 1H NMR (MeOD): δ 8.55 (s, 1H), 8.35-8.41 (m, 3H), 7.71-7.76 (m, 2H). MS m/z 288.9 (M+1).

D: 1-Ethyl-6-(3-trifluoromethyl-phenyl)-1H-imidazo[4,5-c]pyridine-4-carbonitrile:

To a stirring solution of 6-(3-trifluoromethyl-phenyl)-1H-imidazo[4,5-c]pyridine-4-carbonitrile (50 mg, 0.17 mmol) in acetonitrile (1 ml) was added cesium carbonate (62 mg, 0.19 mmol) and iodoethane (15 µl, 0.19 mmol). The resulting suspension was stirred at room temperature overnight. Reaction mixture was diluted with dichloromethane (5 ml) and water (5 ml) and filtered through a hydrophobic frit and concentrated in vacuo. Residual orange oil was triturated with ether (5 ml) and resulting precipitate was filtered and dried to give the title compound as a pale yellow solid (4 mg). 1H NMR (MeOD): δ 8.56 (s, 1H), 8.52 (s, 1H), 8.46 (s, 1H), 8.41 (d, 1H), 7.71-7.74 (m, 2H), 4.46-4,51 (q, 2H), 1.57-1.61 (t, 3H). MS m/z 317.0 (M+1).

EXAMPLE 13a 6-(4-Ethoxy-3-trifluoromethyl-phenyl)-2-(pyridin-3-ylaminomethyl)-1H-imidazo[4,5-c]pyridine-4-carbonitrile

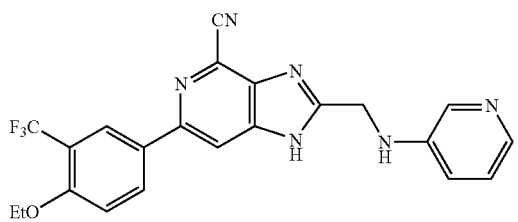

A solution of 2-chloromethyl-6-(4-ethoxy-3-trifluoromethyl-phenyl)-1H-imidazo[4,5,c]pyridine-4-carbonitrile (20 mg, 0.052 mmol), diisoproplylethylamine (28.4 uL,0.16 mmol) and 3-aminopyridine (9.8 mg, 0.1 mmol) dimethylsulfoxide (500 μL) was heated in the Creator microwave at 120° C. for 5 minutes. The mixture was filtered and purified by preparative HPLC to afford the title compound. $^1$H NMR (MeOH) δ 8.3-8.2 (m, 5H), 7.76-7.74 (m, 2H), 7.27 (d, 1H), 6.07 (s, 2H) 4.23 (q, 2H) 1.45 (t, 3H) MS m/z 439.1 (m+1).

The procedure described above was further applied, using the appropriate amine derivatives, to prepare the following compounds:

13b: 6-(4-Ethoxy-3-trifluoromethyl-phenyl)-2-(pyridin-2-ylaminomethyl)-1H-imidazo-[4,5-c]pyridine-4-carbonitrile $^1$H NMR (MeOH) δ 8.33-8.23 (m, 3H) 8.08 (d, 1H), 8.00 (t, 1H) 7.30 (d, 1H) 7.22 (d, 1H) 7.01 (t, 1H) 5.83 (s, 2H), 4.24 (q, 2H) 1.46 (t, 3H) MS m/z 439.1 (m+1)

13c: N-(2-{[4-Cyano-6-(4-ethoxy-3-trifluoromethyl-phenyl)-1H-imidazo[4,5-c]pyridin-2-ylmethyl]-amino}-ethyl)-methanesulfonamide $^1$H NMR (MeOH) δ 8.32-8.28 (m, 3H) 7.30 (d, 2H) 4.72 (s, 2H) 4.25 (q, 2H) 3.56-2.96 (m, 4H) 3.04 (s, 3H) 1.46 (q, 3H) MS m/z 483.5 (m+1)

13d: 6-(4-Ethoxy-3-trifluoromethyl-phenyl)-2-(4-oxo-imidazolidin-1-ylmethyl)-1H-imidazo[4,5-c]pyridine-4-carbonitrile $^1$H NMR (DMSO) δ 8.37-8.26 (m, 3H) 8.21 (s, 1H) 7.40 (d, 1H) 4.27 (q, 2H), 4.20 (s, 2H), 4.15 (s, 2H) 1.38 (t, 3H) MS m/z 431.9 (m+1)

13e: 2-[4-(2-Dimethylamino-ethyl)-3-oxo-piperazin-1-ylmethyl]-6-(4-ethoxy-3-trifluoromethyl-phenyl)-1H-imidazo[4,5-c]pyridine-4-carbonitrile $^1$H NMR (MeOH) δ 8.31-8.25 (m, 2H) 8.20 (s, 1H) 7.28 (d, 1H) 4.23 (q, 2H), 4.07 (s, 2H) 3.78 (t, 2H) 3.52 (t, 2H) 3.42-3.35 (m, 4H) 2.98 (m, 8H) 1.46 (t, 3H) MS m/z 516.3 (m+1)

13f: 6-(4-Ethoxy-3-trifluoromethyl-phenyl)-2-[4-(2-hydroxy-ethyl)-3-oxo-piperazin-1-yl-methyl]-1H-imidazo[4,5-c]pyridine-4-carbonitrile $^1$H NMR (MeOH) δ 8.31-8.24 (m, 2H) 8.18 (s, 1H) 7.28 (d, 1H) 4.23 (q, 2H) 4.16 (s, 2H) 3.74 (t, 2H)3.61 (t, 2H) 3.54 (t, 2H) 3.47 (s, 2H) 3.06 (t, 2H) 1.46 (tm 3H) MS m/z 489.4 (m+1)

13g: 6-(4-Ethoxy-3-trifluoromethyl-phenyl)-2-(3,3,4-trimethyl-piperazin-1-ylmethyl)-1H-imidazo[4,5-c]pyridine-4-carbonitrile $^1$H NMR (MeOH) δ 8.27 (s, 1H), 8.25 (d, 1H) 8.16 (s, 1H) 7.24 (d, 1H) 4.23 (q, 2H) 3.99 (s, 2H) 3.41-3.35 (bm, 2H) 3.19-3.10 (bm, 2H) 2.98-2.0 (bm, 1H) 2.82 (s, 3H) 2.69-2.59 (bm, 1H) 2.57-2.48 (bm, 1H) 1.50-1.40 (m, 9H) MS m/z 473.5 (m+1)

13h: 2-{[(5-Dimethylaminomethyl-furan-2-ylmethyl)-amino]-methyl}-6-(4-ethoxy-3-trifluoromethyl-phenyl)-1H-imidazo[4,5-c]pyridine-4-carbonitrile $^1$H NMR (MeOH) δ 8.36-8.28 (m, 3H) 7.29 (d, 2H), 7.05 (d, 1H) 6.73 (d, 1H) 5.00 (s, 2H) 4.98 (s, 2H) 4.27-4.22 (m, 4H) 3.34-3.30 (m, 6H) 1.46 (t, 3H) MS m/z 499.6 (m+1).

13i: 6-(4-Ethoxy-3-trifluoromethyl-phenyl)-2-[4-(2-methoxy-ethyl)-piperazin-1-yl-methyl]-1H-imidazo[4,5-c]pyridine-4-carbonitrile $^1$H NMR (MeOH) δ 8.28 (s, 1H) 8.25 (d, 1H) 8.16 (s, 1H) 7,27 (d, 1H) 4.24 (q, 2H) 4.04 (s, 2H) 3.74 (t, 2H) 3.65-3.2 (bm, 8H) 3.15-2.6 (bm, 4H) 1.46 (t, 3H) MS m/z 489.5 (m+1)

13j 6-(4-Ethoxy-3-trifluoromethyl-phenyl)-2-[4-(3-hydroxy-propyl)-piperazin-1-yl-methyl]-1H-imidazo[4,5-c]pyridine-4-carbonitrile $^1$H NMR (MeOH) δ 8.28 (s, 1H) 8.25 (d, 1H) 8.16 (s, 1H) 7,27 (d, 1H) 4.24 (q, 2H) 4.05 (s, 2H) 3.7 (t, 2H) 3.7-3.4 (bm, 2H) 3.4-2.55 (bm, 6H) 1.96 (m, 2H) 1.46 (t, 3H) MS m/z 489.5 (m+1)

13k: 2-{4-[4-Cyano-6-(4-ethoxy-3-trifluoromethyl-phenyl)-1H-imidazo[4,5-c]pyridin-2-ylmethyl]-piperazin-1-yl}-isopropyl-acetamide $^1$H NMR (MeOH) δ 8.28 (s, 1H), 8.27 (d, 1H), 8.17 (s, 1H), 7.27 (d, 1H) 4.23 (q, 2H) 4.08 (s, 2H) 4.02 (m, 1H) 3.89 (s, 2H) 3.44 (bs, 4H) 3.29 (bs, 4H) 1.46 (t, 3H) 1.18 (d, 6H) MS m/z 530.3 (m+1)

13l: 6-(4-Ethoxy-3-trifluoromethyl-phenyl)-2-[4-(2-hydroxy-ethyl)-piperazin-1-yl-methyl]-1H-imidazo[4,5-c]pyridine-4-carbonitrile $^1$H NMR (MeOH) δ 8.28 (s, 1H), 8.26 (d, 1H), 8.16 (s, 1H), 7.24 (d, 1H) 4.23 (q, 2H) 4.05 (s, 2H) 3.90 (t, 2H) 3.65-2,65 (bm, 10H) 1.46 (t, 3H) MS m/z 475.5 (m+1)

13m: 2-{[(2-Dimethylamino-ethyl)-methyl-amino]-methyl}-6-(4-ethoxy-3-trifluoromethyl-phenyl)-1H-imidazo[4,5-c]pyridine-4-carbonitrile $^1$H NMR (MeOH) δ 8.30 (s, 1H) 8.25 (d, 1H) 8.22 (1, 1H) 7.29 (d, 1H) 4.24 (q, 2H) 4.11 (s, 2H) 3.38 (t, 2H) 3.03 (m, 8H) 2.50 (s, 3H) 1.46 (t, 3H) MS m/z 447.5 (m+1)

13n: 6-(4-Ethoxy-3-trifluoromethyl-phenyl)-2-(4-isopropyl-piperazin-1-ylmethyl)-1H-imidazo[4,5-c]pyridine-4-carbonitrile $^1$H NMR (MeOH) δ 8.26 (s, 1H) 8.21 (d, 1H) 8.14 (s, 1H) 7.25 (d, 1H) 4.22 (q, 2H) 4.04 (s, 3H) 3.59-3.39 (m, 3H) 3.31-3.12 (bm, 4H) 2.81-2,64 (bm, 2H) 1.46 (t, 3H) 1.39 (d, 6H) MS m/z 473.5 (m+1)

13o: 6-(4-Ethoxy-3-trifluoromethyl-phenyl)-2-(4-methyl-[1,4]diazepan-1-ylmethyl)-1H-imidazo[4,5-c]pyridine-4-carbonitrile $^1$H NMR (MeOH) δ 8.29 (s, 1H) 8.25 (d, 1H) 8.19 (s, 1H) 7.28 (d, 1H) 4.26-4.21 (m, 4H) 3.53-3.46 (bm, 4H) 3.19 (t, 2H) 3.00 (t, 2H) 2.97 (s, 3H) 2.13 (m, 2H) 1.46 (t, 3H) MS m/z 459.6 (m+1)

13p: 6-(4-Ethoxy-3-trifluoromethyl-phenyl)-2-(1-oxo-1λ$^4$-thiomorpholin-4-ylmethyl)-1H-imidazo[4,5-c]pyridine-4-carbonitrile $^1$H NMR (MeOH) δ 8.28-8.24 (m, 2H), 8.17 (s, 1H) 7.28 (d, 2H) 4.23 (q, 3H) 3.48-3.36 (m, 2H) 3.20-3.00 (m, 6H) 1.46 (t, 3H) MS m/z 464.3 (m+1)

13q: 2-(1,1-Dioxo-1λ$^6$-thiomorpholin-4-ylmethyl)-6-(4-ethoxy-3-trifluoromethyl-phenyl)-1H-imidazo[4,5-c]pyridine-4-carbonitrile $^1$H NMR (DMSO) δ 8.39-8.25 (m, 3H) 7.40 (d, 1H) 4.26 (q, 2H) 4.11 (s, 2H) 3.18 (m, 4H) 3.08 (m, 4H) 1.36 (q, 3H) MS m/z 480.3 (m+1)

EXAMPLE 14

6-(4-Ethoxy-3-trifluoromethyl-phenyl)-2-(3-morpholin-4-yl-propyl)-1H-imidazo[4,5-c]pyridine-4-carbonitrile

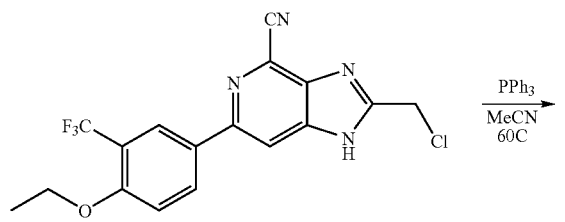

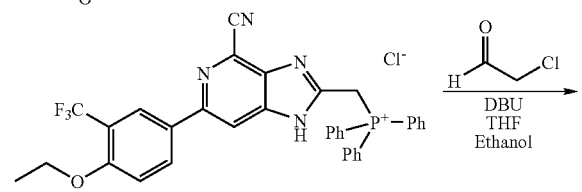

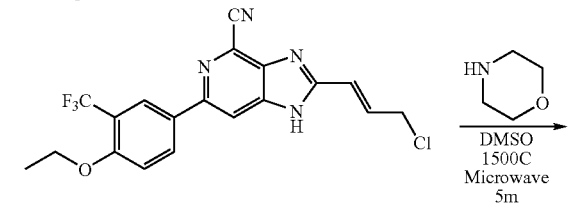

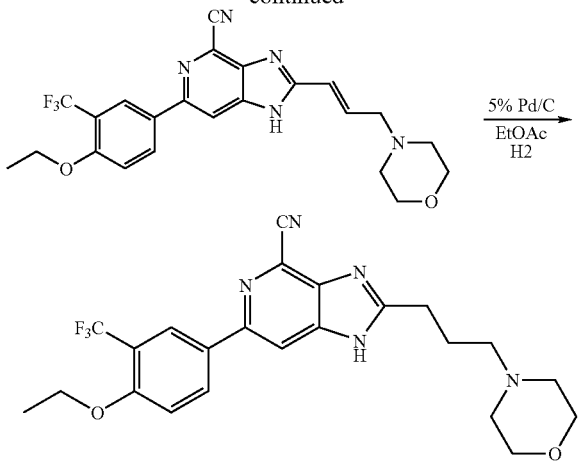

A: [4-Cyano-6-(4-ethoxy-3-trifluoromethyl-phenyl)-1H-imidazo[4,5-c]pyridin-2-yl-methyl]-triphenyl-phosphonium chloride 2-Chloromethyl-6-(4-ethoxy-3-trifluoromethyl-phenyl)-1H-imidazo[4,5,c]-pyridine-4-carbonitrile (100 mg, 0.26 mmol) and triphenylphosphine in acetonitrile were heated to 60° C. and stirred overnight. The reaction mixture was concentrated and triturated with ether to give a light yellow solid. MS m/z 607.5 (m).

B: 2-(3-Chloro-propenyl)-6-(4-ethoxy-3-trifluoromethyl-phenyl)-1H-imidazo[4,5-c]pyridine-4-carbonitrile A solution of [4-cyano-6-(4-ethoxy-3-trifluoromethyl-phenyl)-1H-imidazo[4,5-c]pyridin-2-ylmethyl]-triphenyl-phosphonium chloride (167.2 mg, 0.26 mmol), chloroacetaldehyde (50% in water) (32,6 mg, 0.41 mmol) and 1,8-diazabicyclo[5.4.0]undec-7-ene (62.4 mg, 0.41 mmol) was dissolved in a 1:1 mixture of THF:ethanol (4 ml) at room temperature overnight. The mixture was concentrated and purified on preparative HPLC to afford the title compound. MS m/z 407.5 (m+1).

C: 6-(4-Ethoxy-3-trifluoromethyl-phenyl)-2-(3-morpholin-4-yl-propenyl)-1H-imidazo-[4,5-c]pyridine-4-carbonitrile A solution of 2-(3-chloro-propenyl)-6-(4-ethoxy-3-trifluoromethyl-phenyl)-1H-imidazo[4,5-c]pyridine-4-carbonitrile (23 mg, 0.05 mmol), morpholine (16.1 mg, 0.15 mmol) in DMSO (500 uL) was heated to 120° C. for 5 minutes. The mixture was purified using ion exchange chromatography to afford the title compound.

MS m/z 458.9 (m+1)

D: 6-(4-Ethoxy-3-trifluoromethyl-phenyl)-2-(3-morpholin-4-yl-propyl)-1H-imidazo[4,5-c]pyridine-4-carbonitrile To a flask containing a solution of 6-(4-ethoxy-3-trifluoromethyl-phenyl)-2-(3-morpholin-4-yl-propenyl)-1H-imidazo[4,5-c]pyridine-4-carbonitrile (16 mg) in ethanol was added 5% Pd/C (5 mg) and the vessel purged with hydrogen. The mixture was stirred for 1 h before filtration and purification by preparatice HPLC to afford the title compound. $^1$H NMR (MeOH) δ 8.32-8.25 (m, 2H) 8.17 (s, 1H) 7.30 (d, 1H) 4.24 (q, 2H) 4.20-3.84 (bm, 4H) 3.65-3.60 (bm, 2H) 3.40 (t, 2H) 3.22 (m, 4H) 2.40 (m, 2H) 1.45 (t, 3H) MS m/z 460.7 (m+1)

EXAMPLE 15a 2-((4-(Pyridin-4-yl)piperazin-1-yl)methyl)-6-(3-(trifluoromethyl)phenyl)-1H-imidazo[4,5-c]pyridine-4-carbonitrile 2,2,2-trifluoroacetate A: 2-(chloromethyl)-6-(3-(trifluoromethyl)phenyl)-1H-imidazo[4,5-c]pyridine-4-carbonitrile To a solution of 3,4-diamino-6-(3-trifluoromethyl-phenyl)-pyridine-2-carbonitrile (1.6 g) and 2-chloro-1,1,1-triethoxyethane (3.41 g,) in acetonitrile (40 ml) was added ytterbium triflate (180 mg, 5 mol %) and the mixture heated to reflux over-night. The mixture was concentrated under reduced pressure before partitioning between ethyl acetate (100 ml) and water (100 ml). The organic layer was dried over sodium sulfate and concentrated before addition of diethylether (20 ml). The precipitate was filtered and dried under a stream of air to afford the title compound. $^1$H NMR (MeOD) δ 8.40 (s, 1H) 8.32-8.38 (m, 2H) 8.13-8.15 (d, 2H) 7.68-7.78 (m, 2H) 4.96 (s, 2H). MS m/z 337.5, 339.1 (M+1).

B: 2-((4-(pyridin-4-yl)piperazin-1-yl)methyl)-6-(3-(trifluoromethyl)phenyl)-1H-imidazo[4,5-c]pyridine-4-carbonitrile 2,2,2-trifluoroacetate A solution of 2-(chloromethyl)-6-(3-(trifluoromethyl)phenyl)-1H-imidazo[4,5-c]pyridine-4-carbonitrile (15 mg, 0.045 mmol) and 1-(4-pyridyl)-piperazine (36 mg, 0.223 mmol) in dimethylsulfoxide (500 μL) was heated in the Creator microwave at 120° C. for 5 minutes. The mixture was filtered and purified by preparative HPLC to afford the title compound. $^1$H NMR (MeOD) δ 8.40 (s, 1H) 8.32-8.34 (m, 2H) 8.13-8.15 (d, 2H) 7.68-7.78 (m, 2H) 7.18-7.2 (d, 2H) 4.11 (s, 2H) 3.82-3.88 (m, 4H) 2.85-2.91 (m, 4H). MS m/z 464.1 (M+1)

The procedure described above was further applied, using the appropriate amine derivatives, to prepare the following compounds:

15b: 2-((2-Hydroxyethylamino)methyl)-6-(3-(trifluoromethyl)phenyl)-1H-imidazo[4,5-c]pyridine-4-carbonitrile 2,2,2-trifluoroacetate $^1$H NMR (MeOD) δ 8.41 (s, 2H) 8.35-8.37 (d, 1H) 7.70-7.77 (m, 2H) 4.73 (s, 2H) 3.92-3.94 (t, 2H) 3.42-3.45 (t, 2H). MS m/s 362.8 (M+1)

15c: 2-((pyridin-4-ylamino)methyl)-6-(3-(trifluoromethyl)phenyl)-1H-imidazo[4,5-c]pyridine-4-carbonitrile 2,2,2-trifluoroacetate $^1$H NMR (MeOD) δ 8.40 (s, 1H) 8.37 (s, 1H) 8.34-8.36 (d, 1H) 8.22-8.24 (m, 2H) 7.71-7.76 (m, 2H) 6.92-6.94 (m, 2H) 5.77 (s, 2H). MS m/z 395.1 (M+1)

EXAMPLE 16a

1-Ethyl-2-(4-methyl-piperazin-1-ylmethyl)-6-(3-trifluoromethyl-phenyl)-1H-imidazo[4,5-c]pyridine-4-carbonitrile bis-trifluoroacetate

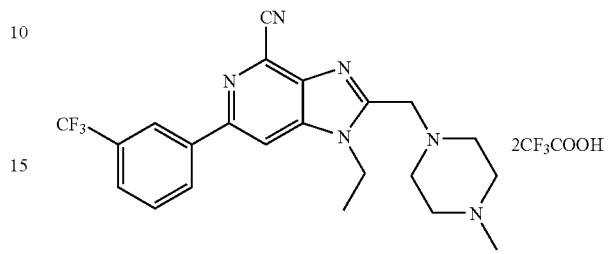

A: 6-Chloro-4-ethylamino-3-nitro-pyridine-2-carbonitrile

At room temperature, potassium carbonate (3.06 g) was added by portions to a solution of 4-amino-6-chloro-3-nitro-pyridine-2-carbonitrile (4.0 g) in DMF (60 mL). A solution of ethyl iodide (3.46 g) in DMF (20 mL) was added dropwise to the mixture, then stirred for 24 h at room temperature and concentrated under reduced pressure. The residue was partitioned between water (50 ml) and ethyl acetate (100 ml). The aqueous layer was extracted with ethyl acetate (2×50 ml). The combined organic layers were washed with brine (3×50 ml), then concentrated under reduced pressure. The residue was chromatographed over silica gel (eluent: dichloromethane) to afford the title compound (2.94 g) as yellow crystals (mp=120° C.). $^1$H NMR (DMSO-$d_6$) δ: 8.67 (br. s, 1H); 7.46 (s, 1H); 3.51 (q, J=8 Hz, 2H); 1.21 (t, J=8 Hz, 3H). MS m/z: 227/229 (M+1).

B: 4-Ethylamino-3-nitro-6-(3-trifluoromethyl-phenyl)-pyridine-2-carbonitrile

Tetrakis(triphenylphosphine)palladium (2.78 g) was added under a nitrogen atmosphere to a mixture of 6-chloro-4-ethylamino-3-nitro-pyridine-2-carbonitrile (10.9 g), 4-trifluoromethyl-phenylboronic acid (10.0 g) in degassed dioxane (500 mL) and a 2M aqueous solution of potassium carbonate (60 mL). The mixture was refluxed for 4 hours then concentrated under reduced pressure. The residue was partitioned between ethyl acetate (300 mL) and water (300 mL). The aqueous layer was extracted with ethyl acetate (2×300 mL). The combined organic layers were washed with brine, dried over sodium sulfate, filtered and concentrated under reduced pressure. The residue was chromatographed over silica gel (eluent: DCM then DCM/acetone 95/5) to afford the title compound (10.4 g, 64%). $^1$H NMR (DMSO-$d_6$) δ: 8.59 (br. s, 1H); 8.50-8.40 (m, 2H); 7.91 (d, J=8 Hz, 1H); 7.79 (t, J=7 Hz, 1H); 7.74 (s, 1H); 3.65 (q, J=7 Hz, 2H); 1.24 (t, J=7 Hz, 3H). MS m/z: 337 (M+1).

C: 3-Amino-4-ethylamino-6-(3-trifluoromethyl-phenyl)-pyridine-2-carbonitrile

At 0° C., a solution of tin chloride dihydrate (30.2 g) in concentrate aqueous HCl (150 mL) was added dropwise over 2 hours to a solution of 4-ethylamino-3-nitro-6-(3-trifluoromethyl-phenyl)-pyridine-2-carbonitrile (5.0 g) in DMF (100 mL). The mixture was further stirred for 1 hour at 5° C., then poured to a mixture of ice (900 g) and potassium hydroxide (440 g), extracted with ethyl acetate (2×1.4 L). The combined organic layers were washed with brine (700 mL), dried over sodium sulfate, filtered and concentrated under reduced pressure to afford the title compound (4,56 g) as a solid. $^1$H NMR (DMSO-d$_6$) δ: 8.30-8.20 (m, 2H); 7.75-7.60 (m, 2H); 7.08 (s, 1H); 6.11 (t, J=6 Hz, 1H); 5.95 (br. s, 2H); 3.4-3.3 (m, 2H); 1.27 (t, J=7 Hz, 3H).

D: 2-Chloromethyl-1-ethyl-6-(3-trifluoromethyl-phenyl)-1H-imidazo[4,5-c]pyridine-4-carbonitrile Ytterbium triflate (1.16 g, 1.8 mmol) and 2-chloro-1,1,1-trimethoxyethane (7.56 mL, 56.0 mmol) was added to a solution of 3-amino-4-ethylamino-6-(3-trifluoromethylphenyl)-pyridine-2-carbonitrile (5.73 g, 18.7 mmol) in acetonitrile (150 mL). The mixture was refluxed for 48 hours, then concentrated under reduced pressure. The residue was partitioned between ethyl acetate and water. The organic layer was dried over sodium sulfate, filtered and concentrated under reduced pressure. The residue was triturated with diethyl ether, filtered off to afford the title compound (5.92 g, 87%) as a solid. $^1$H NMR (DMSO-d$_6$) δ: 8.85 (s, 1H); 8.50-8.00 (m, 2H); 7.90-7.70 (m, 2H); 5.26 (s, 2H); 4,55-4.45 (m, 2H); 1.48 (t, J=7 Hz, 3H). MS m/z: 365 (M+1).

E: 1-Ethyl-2-(4-methyl-piperazin-1-ylmethyl)-6-(3-trifluoromethyl-phenyl)-1H-imidazo[4,5-c]pyridine-4-carbonitrile bis-trifluoroacetate 1-Methylpiperazine (30 mg) was added to a solution of triethylamine (76 μL) and 2-chloromethyl-1-ethyl-6-(3-trifluoromethyl-phenyl)-1H-imidazo[4,5-c]pyridine-4-carbonitrile (0.100 g) in acetonitrile (4 mL). The mixture was stirred at room temperature for 16 hours, then concentrated under reduced pressure. The residue was chromatographed by preparative HPLC (eluent: H$_2$O+0.05% TFA/CH$_3$CN+0.05% TFA) to afford the title compound (156 mg). $^1$H NMR (MeOD$_4$) δ: 8.53 (s, 1H); 8.48 (s, 1H); 8.42 (d, J=8 Hz, 1H); 7.80-7.70 (m, 2H); 4,58 (q, J=7 Hz, 2H); 4.10 (s, 2H); 3.6-3.4 (m, 2H); 3.3-3.1 (m, 4H); 2.94 (s, 3H); 2.8-2,6 (m, 2H); 1.57 (t, J=7 Hz, 3H). MS m/z: 429 (M+1).

Using the same experimental procedure the following compounds were prepared:

16b: 1-Ethyl-2-(4-pyridin-4-yl-piperazin-1-ylmethyl)-6-(3-trifluoromethyl-phenyl)-1H-imidazo[4,5-c]pyridine-4-carbonitrile bis-trifluoroacetate $^1$H NMR (MeOD$_4$) δ: 8.58 (s, 1H); 8.52 (s, 1H); 8.45 (d, J=8 Hz, 1H); 8.19 (d, J=8 Hz, 2H); 7.80-7.65 (m, 2H); 7.23 (d, J=8 Hz, 2H); 4.64 (q, J=7 Hz, 2H); 4.17 (s, 2H); 3.75-3.65 (m, 4H); 2.80-2,65 (m, 4H); 1.61 (t, J=7 Hz, 3H).

16c: 2-[(Cyclopropylmethyl-amino)-methyl]-1-ethyl-6-(3-trifluoromethyl-phenyl)-1H-imidazo[4,5-c]pyridine-4-carbonitrile trifluoroacetate $^1$H NMR (MeOD$_4$) δ: 8.63 (s, 1H); 8.53 (s, 1H); 8.48 (d, J=8 Hz, 1H); 7.70-7.60 (m, 2H); 4.84 (s, 2H); 4,52 (q, J=7 Hz, 2H); 3.24 (d, J=8 Hz, 2H); 1.55 (t, J=7 Hz, 3H); 1.35-1.20 (m, 1H); 0.85-0.75 (m, 2H); 0.55-0.50 (m, 2H). MS m/z : 400 (M+1).

16d: 1-Ethyl-2-(pyridin-4-ylaminomethyl)-6-(3-trifluoromethyl-phenyl)-1H-imidazo[4,5-c]pyridine-4-carbonitrile 4-Aminopyridine (26 mg, 0.27 mmol) was added to a solution of diisopropylethylamine (0.24 mL, 1.37 mmol) and 2-chloromethyl-1-ethyl-6-(3-trifluoromethy-phenyl)-1H-imidazo[4,5-c]pyridine-4-carbonitrile (0.100 g, 0.27 mmol) in DMF (3 mL). The mixture was heated at 80° C. for 2 hours, than filtered. The precipitate was washed with water, then isopropyl ether, dried to afford the title compound (55 mg, 47%) as a solid (mp=340° C.). $^1$H NMR (DMSO-d$_6$) δ: 8.84 (s, 1H); 8.6-8.5 (m, 2H); 8.31 (d, J=8 Hz, 2H); 7.9-7.7 (m, 2H); 6.97 (d, J=8 Hz, 2H); 5.98 (s, 2H); 4.51 (q, J=7 Hz, 2H); 1.45 (t, J=7 Hz, 3H). MS m/z: 423 (M+1).

16e: 2-(2(R,S)-Cyclohexyl-pyrrolidin-1-ylmethyl)-1-ethyl-6-(3-trifluoromethyl-phenyl)-1H-imidazo[4,5-c]pyridine-4-carbonitrile $^1$H NMR (CDCl$_3$) δ: 8.3-8.2 (m, 2H); 7.88 (s, 1H); 7.69 (d, J=8 Hz, 1H); 7.64 (t, J=8 Hz, 1H); 4.7-4.4 (m, 2H); 4.22 (d, J=14 Hz, 1H); 3.82 (d, J=14 Hz, 1H); 2.7-2.6 (m, 1H); 2.5-2.3 (m, 2H); 1.9-1.4 (m, 13H); 1.2-0.9 (m, 5H). MS m/z: 482(M+1).

16f: 2-(4-Cyclopropanecarbonyl-[1,4]diazepan-1-ylmethyl)-1-ethyl-6-(3-trifluoromethyl-phenyl)-1H-imidazo[4,5-c]pyridine-4-carbonitrile $^1$H NMR (CDCl$_3$) δ: 8.3-8.2 (m, 2H); 7.89 (s, 1H); 7.69 (d, J=8 Hz, 1H); 7.63 (t, J=8 Hz, 1H); 4.55-4.45 (m, 2H); 4.1-4.0 (m, 2H); 3.8-3.6 (m, 4H); 2.95-2.75 (m, 4H); 1.95-1.85 (m, 2H); 1.75-1.65 (m, 1H); 1.54 (t, J=7 Hz, 3H); 1.05-0.95 (m, 2H); 0.8-0.7 (m, 2H). MS m/z: 497 (M+1).

EXAMPLE 17a

1-Ethyl-6-(3,4-dichlorophenyl)-1H-imidazo[4,5-c]pyridine-4-carbonitrile

A: 3-Amino-6-chloro-4-ethylamino-pyridine-2-carbonitrile

At 0° C., a solution of tin chloride dihydrate (25.9 g) in concentrate aqueous HCl (76 mL) was added dropwise over 40 minutes to a solution of 6-chloro-4-ethylamino-3-nitro-pyridine-2-carbonitrile (2.9 g) in DMF (70 mL). The mixture was stirred for 2.5 hours, then poured to a mixture of ice (400 g) and 50% potassium hydroxide (400 mL), extracted with ethyl acetate (3×100 ml). The combined organic layers were washed with 2N sodium hydroxide (700 mL), then brine (3×100 mL), dried over sodium sulfate, filtered and concentrated under reduced pressure. The residue was chromatographed over silica gel (eluent: dichloromethane/ethyl acetate 9/1) to afford the title compound (2.0 g) as white crystals (mp=150° C.). $^1$H NMR (DMSO-d$_6$) δ: 6.46 (s, 1H); 6.42 (br.s, 1H); 6.02 (br.s, 2H); 3.20 (q, J=8 Hz, 2H); 1.26 (t, J=8 Hz, 3H). MS m/z: 197/199 (M+1).

B: 6-Chloro-1-ethyl-1H-imidazo[4,5-c]pyridine-4-carbonitrile

Ytterbium triflate (75 mg) was added to a solution of 3-amino-6-chloro-4-ethyl-amino-pyridine-2-carbonitrile (1.41 g) in triethyl orthoformate (50 mL). The mixture was heated at 120° C. under stirring for 2.5 hours, than concentrated under reduced pressure. The residue was chromatographed (eluent: dichloromethane/ethyl acetate 9/1) to yield a solid which was triturated with diethyl ether and filtered off to afford the title compound (0.973 g, 66%) as white crystals (mp=138° C.). $^1$H NMR (CDCl$_3$) δ: 8.17 (s, 1H); 7.62 (s, 1H); 4.31 (q, J=8 Hz, 2H); 1.62 (t, J=8 Hz, 3H). $^{13}$C NMR (CDCl$_3$) δ: 147.5, 143.8, 142.9, 141.7, 124.0, 114.1, 109.2, 40.9, 15.2.

C: 1-Ethyl-6-(3,4-dichlorophenyl)-1H-imidazo[4,5-c]pyridine-4-carbonitrile

Tetrakis(triphenylphosphine)palladium (15 mg) was added under a nitrogen atmosphere to a mixture of 6-chloro-1-ethyl-1H-imidazo[4,5-c]pyridine-4-carbonitrile (42 mg), 3,4-dichloro-phenylboronic acid (152 mg) and cesium fluoride (100 mg) in DME (2mL) and methanol (1 mL). The mixture was heated at 80° C. for 24 hours then filtered. The filtrate was concentrated under reduced pressure. The residue was purified by using preparative LC/MS (eluent: A: NH$_4$HCO$_3$ 10 mM/B: CH$_3$CN). to afford the title compound (30 mg) as a white solid. $^1$H NMR (CDCl$_3$) δ: 8.20-8.15 (m, 2H); 7.94 (d, J=8 Hz, 1H); 7.91 (s, 1H); 7.58 (d, J=8 Hz, 1H); 4.37 (q, J=7 Hz, 2H); 1.65 (t, J=7 Hz, 3H). MS m/z: 317/ 319 (M+1).

The above described procedure was applied using the appropriate boronic acid derivatives for the synthesis of the following derivatives.

17b: 1-Ethyl-6-(4-chloro-3-trifluoromethyl-phenyl)-1H-imidazo[4,5-c]pyridine-4-carbonitrile $^1$H NMR (CDCl$_3$) δ: 8.36 (s, 1H); 8.23 (d, J=8 Hz, 1H); 8.19 (s, 1H); 7.95 (s, 1H); 7.65 (d, J=8 Hz, 1H); 4.39 (q, J=7 Hz, 2H); 1.66 (t, J=7 Hz, 3H). MS m/z: 351/353 (M+1).

17c: 1-Ethyl-6-(3,5-dichloro-phenyl)-1H-imidazo[4,5-c]pyridine-4-carbonitrile $^1$H NMR (MeOD$_4$) δ: 8.59 (s, 1H); 8.55 (s, 1H); 8.17 (s, 2H); 7.52 (s, 1H); 4.47 (q, J=7 Hz, 2H); 1.58 (t, J=7 Hz, 3H). MS m/z: 1569 317/319 (M+1).

EXAMPLE 18

6-(2-Ethoxy-5-trifluoromethyl-phenyl)-1H-imidazo[4,5-c]pyridine-4-carbonitrile

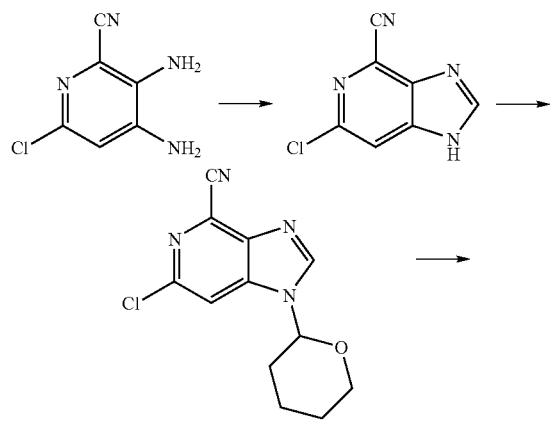

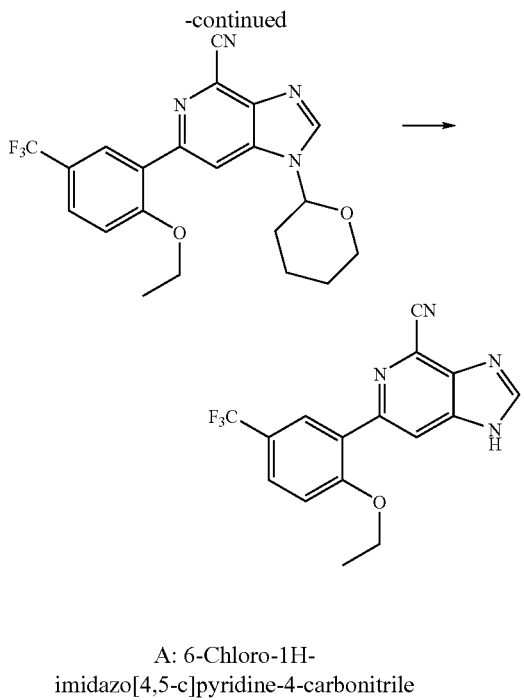

A: 6-Chloro-1H-imidazo[4,5-c]pyridine-4-carbonitrile

This compound was synthesised in the same way as for compound 17a step B starting from 6-chloro-3,4-diamino-pyridine-2-carbonitrile. $^1$H NMR (DMSO) δ: 8.72 (s, 1H), 8.06 (s, 1H).

B: 6-Chloro-2-tetrahydropyranyl-1H-imidazo[4,5-c]pyridine-4-carbonitrile

6-Chloro-1H-imidazo[4,5-c]pyridine-4-carbonitrile (1 g) was dissolved in ethyl acetate (20 ml). To above solution was added 3,4-dihydro-2H-pyran (1 ml) and tosylic acid hydrate (50 mg). The mixture was heated at 60° C. for 10 hours, than washed with sodium bicarbonate (5%, 10 mL). The organic layer dried over sodium sulphate, solvent removed to give the title compound. $^1$H NMR (DMSO) □ 8.92 (s, 1H), 8.30 s, 1H), 5.81 (d, 1H), 4.00 (m, 1H), 3.78 (m, 1H), 2.18 (m, 1H), 2.07 (m, 1H), 1.67 (m, 4H).

C: 6-(2-Ethoxy-5-trifluoromethyl-phenyl)-1-(tetrahydro-pyran-2-yl)-1H-imidazo[4,5-c]pyridine-4-carbonitrile A flask containing 6-chloro-1-(tetrahydro-pyran-2-yl)-1H-imidazo[4,5-c]-pyridine-4-carbonitrile (60 mg), (2-ethoxy-5-trifluomethylphenyl)boronic acid (59.2 mg), tris(dibenzylideneacetone)dipalladium(O) (10.5 mg), tricyclohexylphosphine (7.7 mg) was sealed and purged with nitrogen before addition of dioxane (615 uL). The mixture was degassed by bubbling nitrogen through the mixture before addition of a solution of potassium phosphate (83.0 mg) in water (305 uL). The mixture was heated to 100C and stirred vigorously overnight. The crude mixture was filtered through a silica pad before addition of ethylacetate (30 ml) and water (50 ml). The ethylacetate layer concentrated before purification on 10 g silica column eluting with 40% ethylacetate/heptane to afford the title compound. MS m/z 417.5 (m+1)

D: 6-(2-Ethoxy-5-trifluoromethyl-phenyl)-1H-imidazo[4,5-c]pyridine-4-carbonitrile 6-(2-Ethoxy-5-trifluoromethyl-phenyl)-1-(tetrahydro-pyran-2-yl)-1H-imidazo-[4,5-c]pyridine-4-carbonitrile (67 mg) and para-toluenesulfonic acid hydrate (10 mg) were added in methanol (5 ml) and DCM (5 ml). The mixture was stirred at room temperature overnight before concentration and purification on preparative HPLC to afford 6-(2-Ethoxy-5-trifluoromethyl-phenyl)-1H-imidazo[4,5-c]pyridine-4-carbonitrile. $^1$H NMR (MeOH) δ 8.55 (s, 1H) 8.48 (s, 1H) 8.15 (s, 1H) 7.70 (d, 1H) 7.29 (d, 1H) 4.26 (q, 2H) 1.46 (t, 3H) MS m/z 333.1 (m+1)

EXAMPLE 19

Cathepsin S Assay Procedure

The inhibitory activity of the compounds of the invention was demonstrated in vitro by measuring the inhibition of recombinant human Cathepsin S as follows: To a 384 well microtitre plate is added 10 μl of a 100 μM solution of test compound in assay buffer (100 mM sodium acetate pH5.5, 5 mM EDTA, 5 mM dithiothreitol) with 10% dimethylsulfoxide (DMSO), plus 20 μl of 250 μM solution of the substrate Z-Val-Val-Arg-AMC (7-amido-coumarine derivative of the tripeptide N-benzyloxycarbonyl-Val-Val-Arg-OH) in assay buffer and 45 μl of assay buffer. 25 μl of a 2 mg/l solution of activated recombinant human cathepsin S, in assay buffer, is then added to the well, yielding a final inhibitor concentration of 10 μM.

Enzyme activity is determined by measuring the fluorescence of the liberated aminomethylcoumarin at 440 nM using 390 nM excitation, at 20 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity). Compounds of the invention typically have a $pIC_{50}$ (negative logarithm of the $IC_{50}$ concentration) for inhibition of human cathepsin S of more than 6. Most compounds of the invention have a $pIC_{50}$ of more than 7, such as exemplified by the compounds of examples 1, 3, 4, 5d, 5g, 9a, 9d, 9f, 10a, 10f, 11a, 11h, 13d, 13l.

EXAMPLE 20

Cathepsin K Assay Procedure

The inhibitory activity of the compounds of the invention was demonstrated in vitro by measuring the inhibition of recombinant human Cathepsin K as follows: To a 384 well microtitre plate is added 5 μl of a 100 μM solution of test compound in assay buffer (100 mM sodium acetate pH5.5, 5 mM EDTA, 5 mM dithiothreitol) with 10% dimethylsulfoxide (DMSO), plus 10 μl of 100 μM solution of the substratre Z-Phe-Arg-AMC (7-amido-coumarine derivative of the dipeptide N-benzyloxycarbonyl-Phe-Arg-OH) in assay buffer and 25 μl of assay buffer. 10 μl of a 1 mg/l solution of activated recombinant human cathepsin K, in assay buffer, is then added to the well, yielding a final inhibitor concentration of 10 μM.

Enzyme activity is determined by measuring the fluorescence of the liberated aminomethylcoumarin at 440 nM using 390 nM excitation, at 10 minutes. Percentage enzyme activity is calculated by comparison of this activity to that of a solution containing no inhibitor. Compounds are subsequently subjected to a dose response curve analysis in order to determine $IC_{50}$ values for active compounds (where $IC_{50}$ is the concentration of test compound causing 50% inhibition of the enzymatic activity). Compounds of the invention typically have a $pIC_{50}$ (negative logarithm of the $IC_{50}$ concentration) for inhibition of human cathepsin K of between 5 and 7.

What is claimed is:
1. A 6-phenyl-1H-imidazo[4,5-c]pyridine-4-carbonitrile derivative having the general Formula I

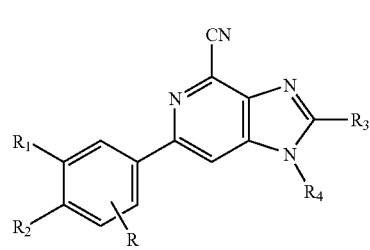

Formula I wherein

R is an optional ortho- or meta-substituent selected from halogen and $(C_{1-4})$alkyloxy;

$R_1$ is $(C_{1-4})$alkyl, $(C_{1-4})$alkyloxy, halogen or $CF_3$;

$R_2$ is H, $(C_{1-4})$alkyl, $(C_{1-4})$alkyloxy or halogen;

$R_3$ is H or $(CH_2)_n$—$NR_5R_6$;

$R_4$ is H or $(C_{1-6})$alkyl, optionally substituted with $COOR_7$ or $NR_8R_9$;

$R_5$ and $R_6$ are independently H, $(C_{3-8})$cycloalkyl, quinuclidin-3-yl, $(C_{2-6})$alkenyl or $(C_{1-6})$alkyl, optionally substituted with halogen, $CF_3$, $(C_{3-8})$cycloalkyl, $(C_{6-10})$aryl, a 5- or 6-membered heteroaryl group, OH, $(C_{1-6})$alkyloxy, $(C_{6-10})$aryloxy, $COOR_{10}$, $CONR_{11},R_{12}$, $NR_{13}R_{14}$ or $NR_{13}SO_2(C_{1-4})$alkyl; or $R_5$ and $R_6$ together with the nitrogen to which they are bound form a 4-8 membered saturated heterocyclic ring, optionally further comprising 1 or more heteroatoms selected from O, S, $SO_2$ and $NR_{15}$, the ring being optionalily substituted with oxo, $(C_{1-4})$alkyl, $(C_{3-8})$cycloalkyl, $NR_{16},R_{17}$ or $CONR_{18},R_{19}$;

$R_7$ is H or $(C_{1-4})$alkyl;

$R_8$ and $R_9$ are independently H, $(C_{1-4})$alkyl (optionally substituted with $di(C_{1-4})$alkylamino) or $(C_{3-8})$cycloalkyl; or $R_8$ and $R_9$ form together with the nitrogen to which they are bound a 4-8-membered saturated heterocyclic ring, optionally further comprising a heteroatom selected from O and S;

$R_{10}$ is H or $(C_{1-4})$alkyl;

$R_{11}$ and $R_{12}$ are independently H or $(C_{1-4})$alkyl; or $R_{11}$ and $R_{12}$ together with the nitrogen to which they are bound form a 4-8 membered saturated heterocyclic ring, optionally further comprising a heteroatom selected from O and S;

$R_{13}$ and $R_{14}$ are independently H or $(C_{1-4})$alkyl; or $R_{13}$ and $R_{14}$ together with the nitrogen to which they are bound form a 4-8 membered saturated heterocyclic ring, optionally further comprising a heteroatom selected from O and S;

$R_{15}$ is H, $(C_{1-4})$alkyl (optionally substituted with OH, $(C_{1-4})$alkyloxy, $di(C_{1-4})$alkylamino, or $CONR_{21},R_{22}$), phenyl, pyridyl, $COR_{20}$ or $CONR_{21},R_{22}$;

$R_{16}$ and $R_{17}$ are independently H or $(C_{1-4})$alkyl; or $R_{16}$ and $R_{17}$ together with the nitrogen to which they are bound form a 4-8 membered saturated heterocyclic ring, optionally further comprising a heteroatom selected from O and S;

$R_{18}$ and $R_{19}$ are independently H or $(C_{1-4})$alkyl;

$R_{20}$ is H, $(C_{1-4})$alkyl, $(C_{3-8})$cycloalkyl, $(C_{1-4})$alkyloxy or furyl;

$R_{21}$ and $R_{22}$ are independently H or $(C_{1-4})$alkyl; or $R_{21}$ and $R_{22}$ together with the nitrogen to which they are bound form a 4-8 membered saturated heterocyclic ring, optionally further comprising a heteroatom selected from O and S; and n is 0 or 1; or a pharmaceutically acceptable salt thereof.

2. The 6-phenyl-1H-imidazo[4,5-c]pyridine-4-carbonitrile derivatives according to Formula I of claim 1, wherein R is absent;

$R_1$ is $(C_{1-4})$alkyl, $(C_{1-4})$alkyloxy or $CF_3$;

$R_2$ is H, $(C_{1-4})$alkyl or $(C_{1-4})$alkyloxy;

$R_3$ is H or $(CH_2)_n$—$NR_5R_6$;

$R_4$ is H or $(C_{1-6})$alkyl, optionally substituted with $COOR_7$ or $NR_8R_9$;

$R_5$ and $R_6$ are independently H, $(C_{3-8})$cycloalkyl, $(C_{2-6})$alkenyl or $(C_{1-6})$alkyl, optionally substituted with halogen, $CF_3$, $(C_{3-8})$cycloalkyl, $(C_{6-10})$aryl, a 5- or 6-membered heteroaryl group, OH, $(C_{1-6})$alkyloxy, $(C_{6-10})$aryloxy, $COOR_{10}$, $CONR_{11}$,$R_{12}$ or $NR_{13}R_{14}$; or $R_5$ and $R_6$ together with the nitrogen to which they are bound form a 4-8 membered saturated heterocyclic ring, optionally further comprising 1 or more heteroatoms selected from O, S, $SO_2$ and $NR_{15}$, the ring being optionally substituted with oxo, $(C_{1-4})$alkyl, $NR_{16}$,$R_{17}$ or $CONR_{18}$,$R_{19}$;

$R_7$ is H or $(C_{14})$alkyl;

$R_8$ and $R_9$ are independently H, $(C_{1-4})$alkyl or $(C_{3-8})$cycloalkyl; or $R_8$ and $R_9$ form together with the nitrogen to which they are bound a 4-8-membered saturated heterocyclic ring, optionally further comprising a heteroatom selected from O and S;

$R_{10}$ is H or $(C_{1-4})$alkyl;

$R_{11}$ and $R_{12}$ are independently H or $(C_{1-4})$alkyl; or $R_{11}$ and $R_{12}$ together with the nitrogen to which they are bound form a 4-8 membered saturated heterocyclic ring, optionally further comprising a heteroatom selected from O and S;

$R_{13}$ and $R_{14}$ are independently H or $(C_{1-4})$alkyl; or $R_{13}$ and $R_{14}$ together with the nitrogen to which they are bound form a 4-8 membered saturated heterocyclic ring, optionally further comprising a heteroatom selected from O and S;

$R_{15}$ is H, phenyl, pyridyl, $COR_{20}$ or $CONR_{21}$,$R_{22}$;

$R_{16}$ and $R_{17}$ are independently H or $(C_{1-4})$alkyl; or $R_{16}$ and $R_{17}$ together with the nitrogen to which they are bound form a 4-8 membered saturated heterocyclic ring, optionally further comprising a heteroatom selected from O and S;

$R_{18}$ and $R_{19}$ are independently H or $(C_{1-4})$alkyl;

$R_{20}$ is H, $(C_{1-4})$alkyl or furyl;

$R_{21}$ and $R_{22}$ are independently H or $(C_{1-4})$alkyl; or $R_{21}$ and $R_{22}$ together with the nitrogen to which they are bound form a 4-8 membered saturated heterocyclic ring, optionally further comprising a heteroatom selected from O and S;

n is 0 or 1;

with the proviso that one of $R_3$ and $R_4$ is H;

or a pharmaceutically acceptable salt thereof.

3. The 6-phenyl-1H-imidazo[4,5-c]pyridine-4-carbonitrile derivative of claim 1, wherein $R_1$ is $CF_3$.

4. The 6-phenyl-1H-imidazo[4,5-c]pyridine-4-carbonitrile derivative of claim 2, wherein $R_1$ is $CF_3$.

5. The 6-phenyl-1H-imidazo[4,5-c]pyridine-4-carbonitrile derivative of claim 1, wherein $R_2$ is $(C_{1-4})$alkyloxy.

6. The 6-phenyl-1H-imidazo[4,5-c]pyridine-4-carbonitrile derivative of claim 2, wherein $R_2$ is $(C_{1-4})$alkyloxy.

7. The 6-phenyl-1H-imidazo[4,5-c]pyridine-4-carbonitrile derivative of claim 3, wherein $R_2$ is $(C_{1-4})$alkyloxy.

8. The 6-phenyl-1H-imidazo[4,5-c]pyridine-4-carbonitrile derivative of claim 4, wherein $R_2$ is $(C_{1-4})$alkyloxy.

9. The 6-phenyl-1H-imidazo[4,5-c]pyridine-4-carbonitrile derivative of claim 5, wherein $R_2$ is ethoxy.

10. The 6-phenyl-1H-imidazo[4,5-c]pyridine-4-carbonitrile derivative of claim 6, wherein $R_2$ is is ethoxy.

11. The 6-phenyl-1H-imidazo[4,5-c]pyridine-4-carbonitrile derivative of claim 7, wherein $R_2$ is ethoxy.

12. The 6-phenyl-1H-imidazo[4,5-c]pyridine-4-carbonitrile derivative of claim 8, wherein $R_2$ is ethoxy.

13. The 6-phenyl-1H-imidazo[4,5-c]pyridine-4-carbonitrile derivative of Formula I of claim 1 which is selected from:

6-(4-ethoxy-3-trifluoromethyl-phenyl)-1H-imidazo[4,5-c]pyridine-4-carbonitrile;

[4-cyano-6-(4-ethoxy-3-trifluoromethyl-phenyl)-imidazo[4,5-c]pyridin-1-yl]-acetic acid;

[4-cyano-6-(4-ethoxy-3-trifluoromethyl-phenyl)-imidazo[4,5-c]pyridin-1-yl]-butyric acid;

6-(4-ethoxy-3-trifluoromethyl-phenyl)-2-(3-oxo-piperazine-1-ylmethyl)-1H-imidazo-[4,5,c]pyridine-4-carbonitrile;

2-(1,1-dioxo-thiazolidin-3-ylmethyl)-methyl]-6-(4-ethoxy-3-trifluoromethyl-phenyl)-1H-Imidazo[4,5-c]pyridine-4-carbonitrile;

6-(4-ethoxy-3-trifluoromethyl-phenyl)-1-(2-morpholin-4-yl-ethyl)-1H-imidazo-[4,5-c]pyridine-4-carbonitrile;

6-(4-ethoxy-3-trifluoromethyl-phenyl)-1-(2-piperidin-1-yl-ethyl)-1H-imidazo-[4,5-c]pyridine-4-carbonitrile;

1-(2-dimethylamino-ethyl)-6-(4-ethoxy-3-trifluoromethyl-phenyl)-1H-imidazo[4,5-c]pyridine-4-carbonitrile;

6-(4-ethoxy-3-trifluoromethyl-phenyl)-1-(3-morpholin-4-yl-propyl)-1H-imidazo[4,5-c]pyridine-4-carbonitrile;

1-(3-dimethylamino-propyl)-6-(4-ethoxy-3-trifluoromethyl-phenyl)-1H-imidazo[4,5-c]pyridine-4-carbonitrile;

6-(4-ethoxy-3-trifluoromethyl-phenyl)-2-(4-methyl-piperazin-1-ylmethyl)-1H-imidazo[4,5-c]pyridine-4-carbonitrile; and 6-(4-ethoxy-3-trifluoromethyl-phenyl)-2-[(2-hydroxyethylamino)-methyl]-1H-imidazo[4,5-c]pyridine-4-carbonitrile;

1-ethyl-2-(pyridin-4-ylaminomethyl)-6-(3-trifluoromethyl-phenyl)-1H-imidazo[4,5-c]pyridine-4-carbonitrile;

6-(4-ethoxy-3-trifluoromethyl-phenyl)-2-[4-(2-hydroxyethyl)-3-oxo-piperazin-1-ylmethyl]-1H-imidazo[4,5-c]pyridine-4-carbonitrile;

6-(4-ethoxy-3-trifluoromethyl-phenyl)-2-(4-oxo-imidazolidin-1-ylmethyl)-1H-imidazo[4,5-c]pyridine-4-carbonitrile;

or a pharmaceutically acceptable salt thereof.

14. A method of treating a disease or disorder selected from myasthenia gravis, and chronic pain in a human, the method comprising administering to the human an effective amount of the 6-phenyl-1H-imidazo[4,5-c]pyridine-4-carbonitrile derivative of claim 1 or a pharmaceutically acceptable salt thereof.

15. The method of claim 14, wherein the 6-phenyl-1H-imidazo[4,5-c]pyridine-4-carbonitrile derivative is selected from:
- 6-(4-ethoxy-3-trifluoromethyl-phenyl)-1H-imidazo[4,5-c]pyridine-4-carbonitrile;
- [4-cyano-6-(4-ethoxy-3-trifluoromethyl-phenyl)-imidazo[4,5-c]pyridin-1-yl]-acetic acid;
- [4-cyano-6-(4-ethoxy-3-trifluoromethyl-phenyl)-imidazo[4,5-c]pyridin-1-yl]-butyric acid;
- 6-(4-ethoxy-3-trifluoromethyl-phenyl)-2-(3-oxo-piperazine-1-ylmethyl)-1H-imidazo-[4,5,c]pyridine-4-carbonitrile;
- 2-(1,1-dioxo-thiazolidin-3-ylmethyl)-methyl]-6-(4-ethoxy-3-trifluoromethyl-phenyl)-1H-Imidazo [4,5-c]pyridine-4-carbonitrile;
- 6-(4-ethoxy-3-trifluoromethyl-phenyl)-1-(2-morpholin-4-yl-ethyl)-1H-imidazo-[4,5-c]pyridine-4-carbonitrile;
- 6-(4-ethoxy-3-trifluoromethyl-phenyl)-1-(2-piperidin-1-yl-ethyl)-1H-imidazo-[4,5-c]pyridine-4-carbonitrile;
- 1-(2-dimethylamino-ethyl)-6-(4-ethoxy-3-trifluoromethyl-phenyl)-1H-imidazo[4,5-c]pyridine-4-carbonitrile;
- 6-(4-ethoxy-3-trifluoromethyl-phenyl)-1-(3-morpholin-4-yl-propyl)-1H-imidazo[4,5-c]pyridine-4-carbonitrile;
- 1-(3-dimethylamino-propyl)-6-(4-ethoxy-3-trifluoromethyl-phenyl)-1H-imidazo[4,5-c]pyridine-4-carbonitrile;
- 6-(4-ethoxy-3-trifluoromethyl-phenyl)-2-(4-methyl-piperazin-1-ylmethyl)-1H-imidazo[4,5-c]pyridine-4-carbonitrile; and
- 6-(4-ethoxy-3-trifluoromethyl-phenyl)-2-[(2-hydroxy-ethylamino)-methyl]-1H-imidazo[4,5-c]pyridine-4-carbonitrile;
- 1-ethyl-2-(pyridin-4-ylaminomethyl)-6-(3-trifluoromethyl-phenyl)-1H-imidazo[4,5-c]pyridine-4-carbonitrile;
- 6-(4-ethoxy-3-trifluoromethyl-phenyl)-2-[4-(2-hydroxy-ethyl)-3-oxo-piperazin-1-ylmethyl]-1H-imidazo[4,5-c]pyridine-4-carbonitrile;
- 6-(4-ethoxy-3-trifluoromethyl-phenyl)-2-(4-oxo-imidazolidin-1-ylmethyl)-1H-imidazo[4,5-c]pyridine-4-carbonitrile;

or a pharmaceutically acceptable salt thereof.

16. The method of claim 14, wherein the disease or disorder is chronic pain.

17. The method of claim 16, wherein the chronic pain is neuropathic pain.

18. A pharmaceutical composition comprising a 6-phenyl-1H-imidazo[4,5-c]pyridine-4-carbonitrile derivative of claim 1, or a pharmaceutically acceptable salt thereof, in admixture with pharmaceutically acceptable auxilliaries.

19. The pharmaceutical composition of claim 18, wherein the 6-phenyl-1H-imidazo[4,5-c]pyridine-4-carbonitrile derivative is selected from:
- 6-(4-ethoxy-3-trifluoromethyl-phenyl)-1H-imidazo[4,5-c]pyridine-4-carbonitrile;
- [4-cyano-6-(4-ethoxy-3-trifluoromethyl-phenyl)-imidazo[4,5-c]pyridin-1-yl]-acetic acid;
- [4-cyano-6-(4-ethoxy-3-trifluoromethyl-phenyl)-imidazo[4,5-c]pyridin-1-yl]-butyric acid;
- 6-(4-ethoxy-3-trifluoromethyl-phenyl)-2-(3-oxo-piperazine-1-ylmethyl)-1H-imidazo-[4,5,c]pyridine-4-carbonitrile;
- 2-(1,1-dioxo-thiazolidin-3-ylmethyl)-methyl]-6-(4-ethoxy-3-trifluoromethyl-phenyl)-1H-Imidazo[4,5-c]pyridine-4-carbonitrile;
- 6-(4-ethoxy-3-trifluoromethyl-phenyl)-1-(2-morpholin-4-yl-ethyl)-1H-imidazo-[4,5-c]pyridine-4-carbonitrile;
- 6-(4-ethoxy-3-trifluoromethyl-phenyl)-1-(2-piperidin-1-yl-ethyl)-1H-imidazo-[4,5-c]pyridine-4-carbonitrile;
- 1-(2-dimethylamino-ethyl)-6-(4-ethoxy-3-trifluoromethyl-phenyl)-1H-imidazo[4,5-c]pyridine-4-carbonitrile;
- 6-(4-ethoxy-3-trifluoromethyl-phenyl)-1-(3-morpholin-4-yl-propyl)-1H-imidazo[4,5-c]pyridine-4-carbonitrile;
- 1-(3-dimethylamino-propyl)-6-(4-ethoxy-3-trifluoromethyl-phenyl)-1H-imidazo[4,5-c]pyridine-4-carbonitrile;
- 6-(4-ethoxy-3-trifluoromethyl-phenyl)-2-(4-methyl-piperazin-1-ylmethyl)-1H-imidazo[4,5-c]pyridine-4-carbonitrile; and
- 6-(4-ethoxy-3-trifluoromethyl-phenyl)-2-[(2-hydroxy-ethylamino)-methyl]-1H-imidazo[4,5-c]pyridine-4-carbonitrile;
- 1-ethyl-2-(pyridin-4-ylaminomethyl)-6-(3-trifluoromethyl-phenyl)-1H-imidazo[4,5-c]pyridine-4-carbonitrile;
- 6-(4-ethoxy-3-trifluoromethyl-phenyl)-2-[4-(2-hydroxy-ethyl)-3-oxo-piperazin-1-ylmethyl]-1H-imidazo[4,5-c]pyridine-4-carbonitrile;
- 6-(4-ethoxy-3-trifluoromethyl-phenyl)-2-(4-oxo-imidazolidin-1-ylmethyl)-1H-imidazo[4,5-c]pyridine-4-carbonitrile;

or a pharmaceutically acceptable salt thereof.

20. The method of claim 14, wherein the disease or disorder is myasthenia gravis.

21. A method of inhibiting cathepsin K or cathepsin S in a human, comprising administering to the human an effective amount of the compound of claim 1 or a pharmaceutically acceptable salt thereof.

* * * * *